United States Patent
Giuffrida et al.

(10) Patent No.: US 10,694,992 B1
(45) Date of Patent: Jun. 30, 2020

(54) DEVICE AND METHOD FOR MONITORING AND ASSESSMENT OF MOVEMENT DISORDER SYMPTOMS

(71) Applicants: Joseph P. Giuffrida, Hinckley, OH (US); Dustin A. Heldman, Shaker Heights, OH (US); Thomas O. Mera, Columbus, OH (US)

(72) Inventors: Joseph P. Giuffrida, Hinckley, OH (US); Dustin A. Heldman, Shaker Heights, OH (US); Thomas O. Mera, Columbus, OH (US)

(73) Assignee: Great Lakes NeuroTechnologies Inc., Cleveland, OH (US)

( * ) Notice: Subject to any disclaimer, the term of this patent is extended or adjusted under 35 U.S.C. 154(b) by 127 days.

(21) Appl. No.: 16/108,746

(22) Filed: Aug. 22, 2018

Related U.S. Application Data

(63) Continuation of application No. 15/210,990, filed on Jul. 15, 2016, now Pat. No. 10,085,689, which is a continuation of application No. 12/818,819, filed on Jun. 18, 2010, now abandoned.

(51) Int. Cl.
 *A61B 5/00* (2006.01)
 *A61B 5/11* (2006.01)
(52) U.S. Cl.
 CPC .......... *A61B 5/4848* (2013.01); *A61B 5/0022* (2013.01); *A61B 5/0077* (2013.01); *A61B 5/1101* (2013.01); *A61B 5/4082* (2013.01); *A61B 5/6826* (2013.01); *A61B 5/742* (2013.01); *A61B 5/7405* (2013.01); *A61B 2562/0219* (2013.01)

(58) Field of Classification Search
 CPC ....... A61B 5/11; A61B 5/1101; A61B 5/4082; A61B 2503/08; A61B 2505/07; A61B 5/4848
 USPC .......................................... 600/595
 See application file for complete search history.

*Primary Examiner* — Deanna K Hall
(74) *Attorney, Agent, or Firm* — Brian Kolkowski

(57) ABSTRACT

The present invention is directed to a device and method for monitoring and assessment of movement disorder symptoms. The device and method disclosed herein are particularly amenable to remote monitoring of a subject's movement disorder symptoms. Briefly stated, in certain preferred embodiments of the present invention the movement disorder monitoring device accompanies a subject to a remote location where the device is used to record data relating to the severity of a subject's movement disorder symptoms over a period of time. This data is then subsequently used by physicians or other clinicians in optimizing and assessing treatment options directed at alleviating a subject's movement disorder symptoms. The method and device of the present invention can be used to monitor symptoms of a number of movement disorders including but not limited to dystonia, essential tremor, Huntington's disease, various ataxias, multiple sclerosis, psychogenic tremor, and Parkinson's disease.

20 Claims, 9 Drawing Sheets

| Intro | Setup Study | Evaluate Study |

Patient ID: 55555  Last Name: Doe  First Name: John ⎯⎯ 800

Tremor
☒ Postural Tremor
☒ Kinetic Tremor
☒ Rest Tremor

Finger Taps
☒ Speed
☒ Amplitude
☒ Rhythm

Hand Grasps
☒ Speed
☒ Amplitude
☒ Rhythm

Rapid Movements
☒ Speed
☒ Amplitude
☒ Rhythm

Dates:
All Dates
04/10/2010
06/12/2010
08/15/2010

- Motor Trends
- Diary Trends
- Time Response
- Interpret
- Create Report

DATE 08/15/2010

| TIME | Rest Tremor | Kinetic Tremor | Postural Tremor | Finger Tap Speed | Finger Tap Amplitude | Finger Tap Rhythm | Hand Grasps Speed | Hand Grasps Amplitude | Hand Grasps Rhythm | Rapid Movements Speed | Rapid Movements Amplitude | Rapid Movements Rhythm |
|---|---|---|---|---|---|---|---|---|---|---|---|---|
| 8:45 AM | 3.4 | 1.3 | 0.1 | 3.5 | 1.5 | 0.3 | 1.5 | 2.0 | 3.1 | 1.5 | 2.7 | 3.6 |
| 9:45 AM | 2.0 | 2.5 | 0.2 | 3.1 | 2.0 | 0.2 | 1.7 | 1.5 | 2.9 | 1.6 | 2.7 | 4.0 |
| 10:45 AM | 2.5 | 1.9 | 0.5 | 3.4 | 1.9 | 0.0 | 1.6 | 2.0 | 3.4 | 1.6 | 2.9 | 2.5 |
| 12:00 PM | 2.7 | 1.4 | 0.3 | 3.5 | 1.8 | 0.5 | 2.0 | 2.0 | 3.6 | 2.4 | 3.1 | 4.0 |
| 1:15 PM | 3.5 | 2.1 | 0.0 | 2.8 | 2.4 | 0.0 | 1.3 | 2.4 | 3.0 | 2.5 | 2.5 | 2.8 |
| 2:30 PM | 2.1 | 1.7 | 0.4 | 3.2 | 3.0 | 0.2 | 1.4 | 1.9 | 2.9 | 2.2 | 2.4 | 3.7 |
| 4:00 PM | 3.5 | 2.0 | 0.1 | 3.2 | 2.8 | 0.4 | 2.4 | 1.8 | 2.9 | 1.9 | 1.0 | 3.5 |
| Mean Score | 2.8 | 1.8 | 0.2 | 3.2 | 2.2 | 0.2 | 1.7 | 1.9 | 3.1 | 2.0 | 2.5 | 3.4 |
| Fluctuation | 0.6 | 0.4 | 0.2 | 0.2 | 3.4 | 0.2 | 0.4 | 3.4 | 3.4 | 3.4 | 3.4 | 0.5 |

Rest Tremor, Left Hand

Symptom Severity ← / Time →

*FIG. 8B*

DEVICE AND METHOD FOR MONITORING AND ASSESSMENT OF MOVEMENT DISORDER SYMPTOMS

CROSS-REFERENCE TO RELATED APPLICATIONS

This application is a continuation of U.S. patent application Ser. No. 15/210,990, which was filed on Jul. 15, 2016 and issued as U.S. Pat. No. 10,085,689 on Oct. 2, 2018, and which is a continuation of U.S. patent application Ser. No. 12/818,819 filed on Jun. 18, 2010, now abandoned.

LICENSE RIGHTS-FEDERAL SPONSORED

The United States Government has a paid-up license in this invention and the right in limited circumstances to require the patent owner to license others on reasonable terms provided for by the terms of grant number 2R44NS043816-04 awarded by the National Institute of Neurological Disorders and Stroke and grant number 1R43MD004049-01 awarded by the National Center on Minority Health and Health Disparities.

BACKGROUND OF THE INVENTION

1. Field of Use

The present invention is directed to a device and method for monitoring and assessment of movement disorder symptoms. The device and method disclosed herein can be used to monitor symptoms of a number of movement disorders including but not limited to dystonia, essential tremor, Huntington's disease, various ataxias, multiple sclerosis, psychogenic tremor, and Parkinson's disease ("PD"). Because PD is one of the most prevalent and life-altering movement disorders, PD will be the central example used in describing the present invention. However, the device and method disclosed herein are equally adaptable for use in monitoring and assessing symptoms of any of the movement disorders mentioned herein or any other movement disorder that involves an inability to control movement of the body's extremities.

Turning now to the specific example of using the present invention to monitor and assess PD symptoms, it is important to note that, as with certain other movement disorders, symptoms of PD frequently fluctuate with time and relative to certain environmental and physiological factors. Because of this fluctuation it is often difficult for clinicians or physicians to adequately quantify the efficacy of treatment measures taken either by a subject or by a physician or clinician to alleviate symptoms of PD. By allowing remote monitoring of fluctuation of PD symptoms over time and by allowing temporally-indexed recording of certain environmental and external factors relative to a subject's measured symptom severity, the present invention allows physicians, clinicians and subjects suffering from PD or another movement disorder to better assess prescribed treatments or other measures taken to alleviate PD symptoms and to more quickly and efficiently optimize such other measures and treatments.

2. Technology Review

As just mentioned, the method and device of the present invention are amenable for use in monitoring a number of movement disorders; however, since PD is currently a very prevalent and life-altering movement disorder, PD will be used as an example in describing the present invention. Parkinson's disease is a neurodegenerative disease that presently affects over 1.5 million people in the United States alone. With an additional 50,000 to 60,000 new cases reported in the U.S. each year, effective management of PD symptoms has become an issue of ever greater concern.

Parkinson's disease is characterized by unnatural motor movements. Most frequently these symptoms are manifested in the form of tremor, bradykinesia and/or rigidity of a subject's upper extremities. However, other symptoms associated with PD include negative effects on gait, balance, speech, olfaction, sleep and cognition. The symptoms associated with Parkinson's disease are the result of the loss of dopamine-producing neurons in the substantia nigra region of the brain. While the exact reason for this neuronal death remains unknown, various treatments have nevertheless been developed to alleviate many of the symptoms of PD.

The most prevalent treatment currently implemented in alleviating PD symptoms is the use of pharmaceutical agents or drugs. While various pharmaceutical agents exist for treatment of PD symptoms, oral administration of L-3,4-dihydroxyphenylalanine ("levodopa" or "L-DOPA") is presently the most common and will thus be the focus of the examples set forth herein. It will further be noted that L-DOPA is often used in combination with (2S)-3-(3,4-dihydroxyphenyl)-2-hydrazino-2-methylpropanoic acid (carbidopa), as a way to further increase L-DOPA bioactivity and decrease L-DOPA side effects. In still other instances, PD may be treated using (R)—N-(prop-2-ynyl)-2,3-dihydro-1H-inden-1-amine (rasagiline). Despite the focus of certain specific examples herein, it is nevertheless to be understood that the present invention is equally adaptable for use with other pharmaceutical agents or drug treatment regimens used with treatment of PD as well as other movement disorders, such as, for example, the use of 5-ethyl-5-phenyl-hexahydropyrimidine-4,6-dione (primidone) or (RS)-1-(isopropylamino)-3-(1-naphthyloxy)propan-2-ol (propanolol) to treat essential tremor, and it is to be understood that all such applications are included within the scope of the present invention.

Levodopa is a dopamine precursor molecule that alleviates PD symptoms by crossing the blood brain barrier and being subsequently converted into dopamine that is used by the body to replace the function of the dopamine that would naturally be found occurring in the body if not for the death of the body's dopaminergic neurons. During treatment, levodopa is typically taken orally by a subject several times per day at intervals specified by a physician. The use of dosage at intervals allows the level of levodopa in the blood to remain somewhat constant throughout the day. However, physiological differences between subjects (e.g. different levels of enzymatic activity, different thresholds for drug efficacy and other like examples) means that there will be no single dosage of levodopa that will be effective for all subjects. It will be appreciated that this same effect is also observed in pharmaceutical treatment of subjects with various other movement disorders besides PD. This lack of uniformity among subjects and the temporal variation of levodopa efficacy in treating PD raise a need for a method and/or device that allows a physician to more optimally titrate a subject's drug regimen based on the drug's effect on a specific subject at specific times and under a subject's specific circumstances.

While treatment with levodopa can improve a subject's PD symptoms in the short-term, such treatment does not come free of side-effects. The most common side-effect resulting from chronic treatment with levodopa is the development of dyskinesias. Such dyskinesias can include irregular brief rapid movements and/or sustained twisting movements depending on the effect of levodopa and the level at which it is present in the body at any given time. Thus, the ability to monitor a subject's PD symptoms over a period of time becomes perhaps even more critical as the duration of treatment with levodopa gets longer.

An additional treatment for PD symptoms often used in conjunction with other treatment methods is that of exercise, as exercise has been shown to alleviate PD symptoms such as tremor and bradykinesia.

Yet another method of PD treatment is the use of deep brain stimulation. Deep brain stimulation involves the implantation of electrodes into a subject's brain and the subsequent use of these electrodes to provide low voltage electrical stimulation to a specific site in a subject's brain as a way to alleviate symptoms of PD as well as other movement disorders such as essential tremor. The mechanism by which electrical stimulation of the brain serves to alleviate PD symptoms is not yet well understood. Importantly, after implantation of the deep brain stimulation system, the system must be "tuned" to produce output parameters (e.g. electrode polarity, amplitude, frequency and pulse width of stimulation) that optimize a subject's response to the treatment. However, this optimal level of stimulation can change with time in response to such factors as a subject's activity level or as the electrodes become encapsulated by fibrous tissue deposited due the body's foreign-body response. Further contributing to variations in the optimal level of stimulation is the fact that the deep brain stimulation tuning process is often also done in conjunction with adjustments to accompanying pharmaceutical therapy. Thus, it is again clear that a method and/or device that allows a physician to monitor a subject's PD symptoms over a time period greater than the time spent in an office visit would provide significant benefits in maintaining an optimal treatment level for a subject over the long-term.

In all of the treatment methods listed above, it is clear that improved outcomes and management of PD symptoms could be achieved if a physician or clinician were able to obtain data on a subject's symptoms beyond that which could be observed in the relatively short time period during which a subject sees a physician or other clinician during a standard office visit. Certainly the same is equally true for any other movement disorder for which treatment and management of the disorder is ongoing. Accordingly, it is an object of the present invention to provide a device and method that allows a physician or clinician to view data on a subject's movement disorder symptoms collected over a period of time and to provide greater insight into treatment efficacy by further allowing a physician or clinician to temporally correlate a subject's symptoms with certain physiological, environmental and other factors as well as the subject's subjective assessment of his or her symptoms.

SUMMARY OF THE INVENTION

The present invention relates to both a device and method for monitoring and assessment of movement disorders and their accompanying symptoms. The device of the present invention is highly amenable to use at locations remote from a physician's office or place of business and is thus advantageous over previous approaches to movement disorder monitoring and assessment as it allows a subject to be both objectively and subjectively monitored over a period of time at a remote location such as in the subject's home. Further, because of its portability and versatility, the device of the present invention is very suitable for use in serving those in rural areas and those who do not have convenient access to healthcare, such as by shipping a device to an individual in a remote area and then having that individual return the device via courier or other means and the individual not needing to first meet with a physician prior to undergoing assessment of movement disorder symptoms.

There are many preferred embodiments of the movement disorder monitoring device of the present invention. However, by way of overview and example, the device of the present invention is generally comprised of a relatively small, portable system that includes at least one movement sensor, a processor, a memory for storing data, a display, and accompanying software for handling, analysis and coordination of data. Importantly, the software of the present invention is often used with other external devices such as personal computers that allow communication of data over the internet and allow access to certain software of the present invention that is stored and run from remote databases.

In certain preferred embodiments, the device of the present invention comprises a sensor, a sensor dock, and a display unit. The sensor can be wired, wireless or a combination of both and is preferably designed to attach to one of a subject's extremities and measure the movement of that extremity. If the sensor used happens to be wireless, it is preferable that a sensor dock is used to store the wireless sensor and, in certain instances, provide a point of data transfer between the wireless sensor and the display unit. The display unit preferably comprises a small screen with at least a processor and memory used to display information to a subject and collect and optionally display data collected from the sensor. In embodiments of the movement disorder monitoring device that do not use a wireless sensor, the sensor can be directly attached to the display unit using a cable or wire. Further, in certain preferred embodiments, one or multiple external systems such as a personal computer can be used to transfer data from the display unit to a remote database using the internet or other communication system for further data analysis and processing at a remote database.

In certain preferred embodiments of the present invention, the display unit is programmable by a physician or other clinician to instruct a subject to perform certain tasks while wearing the sensor of the device at certain times and over a certain duration. In this way the physician or other clinician can control the type of data acquired and ensure that such data collection is tailored to the physician's or other clinician's specific desires or needs.

The method of the present invention spans a number of different preferred embodiments but generally involves various uses of the device disclosed herein to conduct remote monitoring of a subject's movement disorder symptoms over a period of time.

By way of example, in a number of preferred embodiments of the method of the present invention, the method involves the general steps of a physician or other clinician programming the movement disorder monitoring device, the movement disorder monitoring device being sent home with a subject, the subject using the movement disorder monitoring device over a period of time, and the subject returning the movement disorder monitoring device with its accompanying data to the physician or other clinician. Each of these steps can be accomplished in various ways as described in greater detail in the description of preferred embodiments below.

In yet other embodiments, it may be preferable that a subject not meet with a physician in order to have a movement disorder monitoring device sent home with the subject. Instead, the subject or, for example, the subject's insurer may have a movement disorder monitoring device sent directly to the subject's home or other remote location (e.g. by courier service) where it is used by the subject over a period of time and then ultimately returned by the subject to the sender or other third party where data can be extracted from the device and subsequently analyzed. Such an approach allows by the physician and the subject to save the time, expense and inconvenience of an initial appointment. This is especially true for those subjects who live in rural areas and who would benefit from, for example, movement disorder monitoring to establish an appropriate symptom "baseline" prior to formally meeting with a physician for a consultation and/or treatment.

Once a movement disorder monitoring device has been used by a subject and returned to a physician, clinician or other third party, the movement disorder data is extracted from the device and the data can then be analyzed and processed using software present on a personal computer in the physician's or other clinician's place of business or the data can be sent to a remote database where it is further processed by a third party and made available to the physician or other clinician through a remotely accessible world wide web portal.

In light of the summary description provided above it will be clear to those of ordinary skill in the art that an object of the present invention is to provide both a device and method that allow for efficient and accurate remote monitoring of a subject's movement disorder symptoms as a way to give physicians, clinicians and other caregivers greater insight into potential treatments and the efficacy of these treatments.

It will further be clear to those of ordinary skill in the art that additional features and advantages of the invention will be set forth in the detailed description that follows, and in part will be readily apparent to those skilled in the art from that description or recognized by practicing the invention as described herein, including the detailed description that follows, the claims, as well as the appended drawings.

It is further to be understood that both the foregoing general description and the following detailed description are merely exemplary of the invention disclosed herein, and are intended to provide an overview or framework for understanding the nature and character of the invention as it is claimed. The accompanying drawings are included to provide a further understanding of the invention, and are incorporated in and constitute a part of this specification. The drawings illustrate a number of exemplary preferred embodiments of the invention and together with the description serve to explain the principles and operation of the invention.

BRIEF DESCRIPTION OF THE FIGURES

FIGS. 8A-B (A) Illustration of a software interface used in programming the movement disorder monitoring device of the present invention; and
  (B) illustration of a report generated from data collected using the movement disorder monitoring device of the present invention.

DESCRIPTION OF THE PREFERRED EMBODIMENTS

Figure 1:
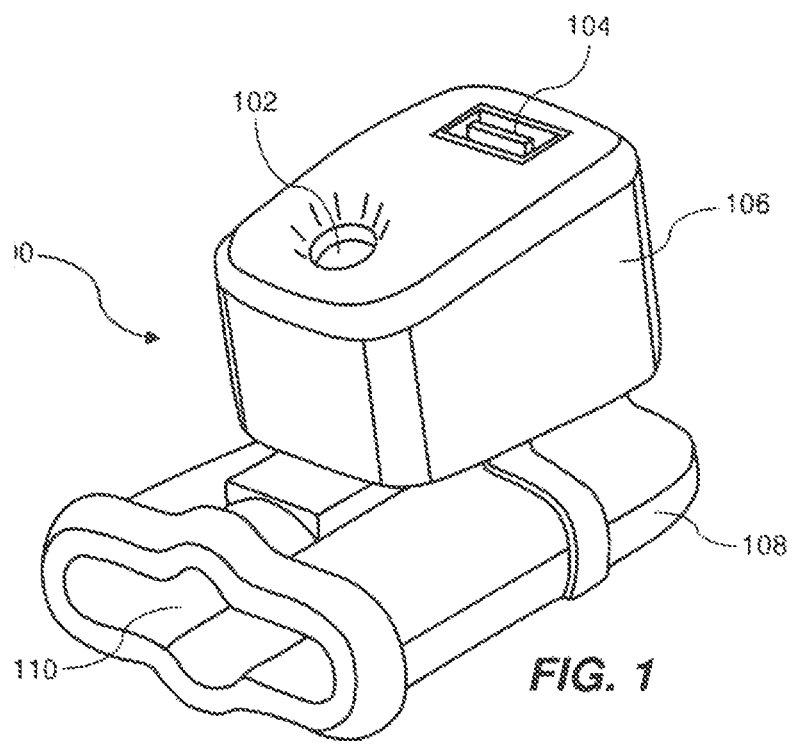
FIG. 1 Perspective drawing of a finger-mounted movement sensor used in certain embodiments of the present invention.

The present invention is directed to a device and method for monitoring and assessment of movement disorder symptoms. More particularly, the present invention involves the use of various methods with a novel movement disorder monitoring device to collect data and allow for remote monitoring of a subject's movement disorder symptoms at locations separate from and independent of a physician's or clinician's office.

The device of the present invention that is used with the various methods included herein generally consists of a number of different physical parts or distinct units. In many preferred embodiments, these parts comprise a movement sensor, a display unit and a sensor dock. Hereinafter, the combination of these parts, including any software that may be present on the various parts, may be referred to as a movement disorder monitoring device. Certain exemplary preferred embodiments of each of the parts of the movement disorder monitoring device are discussed in greater detail below.

Various preferred embodiments of the present invention include the use of a sensor for measuring movement of a subject's extremities. While this sensor can take many forms, it is preferably a small, lightweight sensor that can be easily attached to one or a number of a subject's extremities for monitoring the movement of these extremities. By small, it is meant that the sensor itself (not including means of attachment to a subject) occupies a volume of less than about 30 cubic centimeters, more preferably less than about 20 cubic centimeters, still more preferably less than about 10 cubic centimeters, and most preferably less than about 5 cubic centimeters. By lightweight it is meant that the sensor itself (not including means of attachment to a subject) weighs less than about 100 grams, more preferably less than about 50 grams, still more preferably less than about 20 grams and most preferably less than about 10 grams. By a subject's extremities it is meant any of a subject's hands, feet, arms, legs, neck and/or head.

The sensor further preferably comprises a strap, a boot, or some other like component that provides a means of attachment of the sensor to a subject's extremity. By way of example, but not limitation, the attachment could be performed by a flexible boot that fits snugly over a subject's finger or could be a hook-and-loop strap that allows attachment to a subject by attaching the sensor to the strap and wrapping the strap around a subject's finger, wrist or ankle. It will be clear to those of ordinary skill in the art that there are many other ways to attach such a sensor to a subject including the use of adhesive methods to attach the sensor directly to a subject's skin as well as rigid ring-type components for attaching the sensor to, for example, a subject's finger.

In using the sensor, as few as one sensor may be attached to a subject or multiple sensors may be attached depending on the underlying purpose of attachment of the sensors and the amount of data that is desired to be collected from a subject. By way of example, in one preferred embodiment, a single movement sensor can be attached to a subject's finger in order to monitor movement of the subject's hand. In still other embodiments, a single sensor could be attached to a finger on each of the subject's hands to monitor movement of both hands simultaneously. It will be appreciated by those of ordinary skill in the art that many other combinations of sensors could be used on any combination of extremities in order to obtain desired data.

The sensor for measuring movement of a subject's extremities preferably can measure movement with six degrees of freedom. This means that the sensor can preferably measure translational movement in the x, y and z axes and can further measure rotational movement about each of these axes in order to provide a complete quantitative measurement of the movement of a subject's extremity(ies). These measurements are preferably done using a combination of accelerometers and gyroscopes capable of measuring translation and rotation along and about the respective axes. Accelerometers and gyroscopes used in the movement sensor can be comprised of any combination of triaxial, biaxial or uniaxial units sufficient to provide translational and rotational measurement in three axes, providing six degrees of freedom. By way of example, one preferred embodiment of the sensor of the present invention uses a single Analog Devices ADXL325 3-Axis ±5 g accelerometer to measure translational movement while using an STMircroelectronics LPR5150AL Dual axis pitch and roll ±1500°/s gyroscope in combination with an STMicroelectronics LY5150ALH ±1500°/s yaw-rate gyroscope to measure rotational movement. It will be clear to those of ordinary skill in the art that there are yet many other combinations of the above-noted types of sensors that will allow for measurement of movement with six degrees of freedom and such other combinations are intended to be included within the scope of the present invention.

In certain embodiments, the sensor of the present invention can be either wired or wireless or some combination of the two. If wired, the sensor would directly connect to an external data acquisition device using various wires, such as by a universal serial bus (USB) or other similar connection, and data would be moved directly from the sensor to the external data acquisition device as the data is collected. If a wireless connection is used, data recorded by the sensor could be moved directly to an external data acquisition device using a wireless connection.

Examples of wireless communication protocols that could be used to communicate between various components of the present invention, including between the sensor and an external data acquisition device such as the display unit discussed below, include communication using frequencies less than about 2.0 GHz such as those of the Wireless Medical Telemetry Bands, in the 608-614 MHz, 1395-1400 MHz, or 1429-1432 MHz ranges, and could also include frequencies above 2.0 GHz such as Bluetooth, or IEEE 802.11 communication protocols. An alternative preferred embodiment of a wireless sensor of the present invention is a sensor that includes its own power source, processor, memory and other components for collecting and storing data for later download or transfer to an external system for further processing and analysis. In this way, the sensor is able to function to collect, store and even process data entirely independently from any external data acquisition device but could later be connected to such a device (either wired or wirelessly) to allow data transfer from the sensor and subsequent in-depth data analysis.

The sensor of the present invention preferably further includes means to communicate with or indicate the status of the sensor to the user of the sensor. By way of example, such means could include a small digital display used to communicate the status of the sensor to the user. In one preferred embodiment, a light emitting diode is used to communicate with the user by lighting the diode in various patterns to communicate certain states of the sensor. For example, the light emitting diode could flash at five-second intervals to communicate to the user that the sensor is actively collecting data or performing some other desired function.

Various embodiments of the present invention further include the use of an external display unit to be used in combination with a movement sensor to, among other things, provide instructions to a user concerning sensor use, allow the user to input data into the device using the display unit as an interface, and to further provide a location for additional storage and/or processing of data collected by a movement sensor. The display unit preferably comprises at least a processor, a memory, a power source, a display screen and various input and output channels for data transfer to and from the display unit.

The display screen can be any type of display screen known to those skilled in the art, but in certain preferred embodiments is a liquid crystal display. Preferably the display screen has a square or rectangular architecture and is sized so as to make the display unit easily portable by a user. To this end, the display screen preferably has a corner-to-corner measurement of less than about 55 centimeters, more preferably less than about 43 centimeters and most preferably less than about 25 centimeters.

Input of data to the display unit by the user can occur in any way commonly known to those skilled in the art including, for example, through a standard external computer mouse and keyboard connected to or associated with the display unit or by the use of a touch-sensitive display screen. The display unit is further preferably configured to accept input from a user or outside source such that it will load and execute various software programs, updates or changes to software already present on the display unit, and/or certain algorithms used in data processing. Loading and transfer of data associated with these elements can be accomplished through various input methods that are well-known to those of ordinary skill in the art including, for example, wirelessly using protocols mentioned above or by use of USB communication or optically-readable disk. In certain other preferred embodiments, the display unit can be connected to the internet and data communicated to and from the display unit using an internet connection. Using the internet allows the advantage of being able to rapidly communicate and transfer data between the display unit and a remote location such as a remote server where in-depth analysis of the data can be performed. Preferably the display unit also includes speakers that can generate sound in response to actions taken by the user, commands received from the software, or other input or output variables. Such sound can be used, for example, to call the attention of a user to a task that must be completed or to indicate the successful completion of a task by the user. In other instances the sound can be used alone or to accompany a video to communicate instructions to a user about, for example, use of the display unit or use of a movement sensor attached to the display unit.

The display unit further preferably includes a camera either integrated with the display unit or attached to the display unit. The camera is preferably used to record or observe a subject as the subject performs certain tasks used to evaluate the subject's movement disorder. In this way, the camera can record data that can be used for later review by a physician or clinician to verify motion sensor data or examine environmental or other factors in greater detail.

In certain embodiments the display unit of the present invention further includes a microphone for recording or transmitting audio signals. The microphone in certain instances may be used to allow a subject to communicate with a remote observer and may be used to monitor a subject's voice for tremor or to record subject feedback or responses to certain tasks required of the subject in conducting certain movement disorder monitoring exams.

In various other embodiments the present invention may further include a sensor dock. The sensor dock allows the aforementioned sensor(s) to be conveniently and reliably connected to the display unit when the sensor(s) is not in use. The sensor dock can assume a number of architectures including standing independently from the display unit, being physically connected to the display unit, or being an existing component of the display unit such as in the form of a continuation of the display unit housing that serves as a sensor dock. Preferably the sensor dock is designed to be easily used and ergonomically accessible to those individuals suffering from movement disorders since individuals with movement disorders often have difficulty controlling fine motor movements of their extremities and more particularly their hands. Further, the sensor dock can preferably be configured to accommodate docking of as few as one sensor or multiple sensors depending upon the needs of a particular user. Connection of the sensor dock to the display unit or other external device can be done using any of the methods previously mentioned herein for connecting devices, such as wired using a USB connection, or wirelessly using Bluetooth or other wireless communication protocol mentioned herein or otherwise known in the art.

Connection between the sensor dock and sensor preferably comprises both a mechanical and an electrical connection. The mechanical connection is preferably accomplished by the use of such methods as specific matching geometries between the sensor and the sensor dock that allow the two to fit together in only a single orientation that holds the sensor in a stable position. In certain embodiments the mechanical connection between the sensor and sensor dock may include a "locking" mechanism that serves to temporarily lock the sensor in place until action is taken by the user to release the sensor, such as by pressing a button that releases the "lock" and frees sensor from the sensor dock. In this way, the sensor dock can serve as a stable storage site for the sensor and can be moved when the sensor is not in use without fear of the sensor falling from the dock or detaching from the dock and becoming damaged by being dropped or some other incident. Further, such a "locking" feature provides a stable arrangement for maintaining a consistent electrical connection between the sensor and the sensor dock.

Electrical connection between the sensor and the sensor dock can be made using various electrical connectors in the sensor dock that are complimentary to those found on the sensor. Examples of electrical connectors that could be used in certain preferred embodiments include standard USB or mini-USB connectors, category 5 cable connectors, various keyed or unkeyed pin connectors, RCA connectors, blade connectors, and the like. Preferably this electrical connection can simultaneously allow data transfer between the sensor and the display unit as well as provide power to the sensor for activities such as recharging the sensor battery.

The sensor dock may contain certain indicators that mechanical and/or electrical connections have successfully been established between the sensor and the sensor dock and/or that a proper connection exists between the sensor dock and the display unit to facilitate data transfer from the sensor or power transfer to the sensor. Such an indicator could be as simple as a light emitting diode or other small light-based indicator that illuminates upon successful connection of the sensor to the sensor dock or the sensor dock to the display unit. More complex embodiments could consist of a small digital display used to indicate successful electrical and mechanical connection or data transfer or to display such information as data transfer rate or the number of minutes the sensor was last used or other similar pertinent data. More specific indicators of mechanical connection could still further include designing of the mechanical connection to provide audible and tactile feedback indicative of proper mechanical connection. By way of example, such designs could include a mechanism whereby the user can feel the sensor snap or lock into place in the sensor dock accompanied by a distinct audible click or pop.

Beyond the physical components mentioned above, various embodiments of the present invention also include a software component. Broadly stated, the software component of the present invention allows coordination between the various parts of the present invention discussed above as well as facilitates input from external sources and data transfer to and from locations and devices involved in executing the method of the present invention. The software component of the present invention can take various forms and, when viewed in context of the invention as a whole, is most frequently spread over a number of different locations and executed at a number of different stations. In certain preferred embodiments of the present invention this is achieved by the display unit having its own software application, a second complimentary software application being run or accessed on a station or stations independent of the display unit, and a third complimentary software application being run on a station or stations at a remote site wherein the third software application is used to more fully analyze and process collected data. It will be recognized, however, that in still other embodiments these processes could be partially consolidated or completely consolidated and performed at a single location on a single processing unit such as the display unit described above or such as a portable personal computer. The various functions performed by the software component of the present invention will become more apparent as different additional aspects of the use of the present invention are discussed below.

When using the display unit of the present invention, the unit must normally first be programmed. By programmed it is meant generally that a software application already existing on the display unit is updated with a new set of parameters and a new set of assignments to execute as specified by a physician or other clinician charged with the task of programming the display unit. Among the programming options available for a physician or other clinician to choose from is the selection of certain movement disorder monitoring tasks to be conducted by a subject when the display unit alarms to notify the subject of the need to complete these tasks or when the subject chooses to complete certain tasks if the subject is allowed to complete tasks on his or her own schedule (i.e. in a subject's using the movement disorder monitoring device as a journal or diary). Among the movement disorder monitoring tasks preferably available to a physician to select from during the programming step are tasks to monitor rest tremor, postural tremor (measured as the subject sits with an arm or arms extended outward), finger tapping (measured as the subject taps index finger with thumb), kinetic tremor (measured in certain embodiments as the subject moves his or her hand, with arm extended, toward and away from the subject's face), hand grasping (measured as subject attempts to rapidly open and close his or her hand(s)) and rapid alternating movement of hands (measured as subject attempts to rapidly rotate the hand clockwise then counterclockwise about the wrist). Other options may include tasks to monitor gait, various forms dyskinesia, a subject's ability to arise from a seated position, and a subject's leg agility (e.g. by measuring a subject's ability to tap his or her heel on the ground in rapid succession).

Programming of the display unit in certain embodiments also includes inputting data about a subject. By way of example, data about a subject input during programming could include a subject's history, a unique subject identification number, subject's symptoms, age, weight, therapies currently being pursued and other similar relevant data. Input of programming parameters can be accomplished in a number of ways including input through the use of a standard keyboard or mouse, a touch-sensitive screen used with a graphical user interface, using a different program to automatically load data using a network connection to a remote database, or any other method commonly known to those of ordinary skill in the art.

It will be noted that in certain embodiments of the present invention the display unit need not be programmed to alert the subject to the need to execute any specific tasks. Rather, the display unit could instead simply be programmed with desired data about a subject and then used to record input from the subject on the schedule chosen by the subject. In this way, the movement disorder monitoring device could serve as a type of journal or diary in which a subject could record his or her symptoms when desired.

In still further preferred embodiments, the display unit could be programmed to alert a subject and direct a subject to perform certain movement disorder symptom assessment tasks while at the same time allowing a subject to still use the system as a type of journal or diary by allowing the subject to record his or her symptoms, both subjectively and objectively with use of a sensor, at times when desired by the subject in addition to times when instructed by the display unit.

By way of example, in one preferred embodiment of the present invention programming of the display unit is done in two steps. The first step involves use of a computer or other processing device that is separate from the display unit and that runs an independent software application that is complimentary to the software existing on the display unit. It will be noted that this independent software application may not actually exist on the separate computer but may simply be temporarily accessed at a remote database using the internet or other communication system and a world wide web browser or other data transfer/data sharing software to display the application and transport data associated with the application. This separate computer and the accompanying software application (whether accessed remotely or locally) are used to allow the physician to select various functions that the physician wishes the display unit to execute and the times at which these functions are to be executed. For example, in one preferred embodiment, the physician can select from programming options of having the display unit periodically instruct a subject or user to perform certain movement disorder evaluation tasks such as hand grasps or tapping of fingers. At this point the physician can also enter subject demographic data such as height, age, weight and the like. When completed, the physician saves a file created using the separate computer and its software application to a USB flash drive or other portable data storage device such as a compact disk, an SD/MMC flash memory card, a portable hard drive or any other device suitable for quickly storing and conveniently physically moving data.

The USB flash drive or other portable data storage device is then inserted into or otherwise connected to the display unit and the software of the display unit recognizes the file saved on the data storage device and uses this file to determine what steps to execute and when to execute them. Thus, if a display unit, a sensor and a sensor dock are subsequently sent home with a subject as part of a remote movement disorder monitoring test, the display unit will sound intermittent alarms and provide instructions to the subject in accordance with the physician's programming selections to aid the subject in performing movement disorder evaluation tasks while wearing the sensor at specified times throughout the day.

Programming by the physician allows the physician to customize the data gathered and gives the physician a more accurate view of how a subject's movement disorder symptoms can fluctuate throughout the day.

In all exchange of information that occurs in the above example and in all other embodiments of the present invention, it is important that information be exchanged securely and in ways that do not improperly disclose a subject's identity. Because of this, in certain preferred embodiments, all personal information of a subject is stored securely at a remote database and is accessible only through a secure network connection wherein both the database and connection protocol are compliant with standards required by the health insurance portability and accountability act (HIPAA). Often, this will require encryption of the data to eliminate the possibility that the data can be read by a third party and many preferred embodiments of the present invention include the use of data encryption.

As indicated in the above example, various embodiments of the present invention involve sending a movement disorder monitoring device home or to another remote location with a subject to be used for movement disorder testing away from a physician's or clinician's place of practice. This step occurs after programming of the display unit as described above. Once the subject arrives home, the movement disorder monitoring device is placed in the subject's home where it may be powered by either a single or multiple on-board batteries or by another power source in the subject's home such as a standard 120 volt alternating current outlet. Once in the home the display unit will, at intermittent times selected by the programming physician or clinician, alert the subject of the need to perform certain movement disorder evaluation tasks. At these times, the display unit may produce a sound, provide a visual alert on its display screen, or a combination of both as a way to alert the subject. In response to the alert the subject will place at least one sensor on his or her extremity(ies) as instructed by the display unit and will proceed to follow other instructions provided regarding how to properly complete certain tasks used to evaluate the severity of the subject's movement disorder symptoms. In certain embodiments, the subject may be video recorded by the camera of the display unit so that a physician can at a later time verify that the tasks were indeed correctly completed. Preferably, the subject will also answer other questions at this time regarding a subject's self-assessment of his or her symptoms and the subject's adherence to and use of treatments prescribed by the subject's physician or another clinician. Such questions may consist of inquiries related to the subject's perception of the present severity of the subject's symptoms, the subject's most recent dose of pharmaceutically-based treatment, the subject's activity level throughout the day, and other similar pertinent information that is desired to be known by the physician to help better understand a subject's symptoms. As noted above, however, in certain other embodiments, the display unit may not be programmed to alert a subject, but instead may simply be left available for a subject to input data regarding his or her symptoms or to select movement disorder assessment tasks to perform from among various options according to the subject's personal preferences and schedule as well as the subject's own subjective view of the severity of his or her symptoms.

By way of a more specific example of the above situation, a physician or other clinician may see a subject for treatment of PD and the subject may indicate to the physician that his or her symptoms associated with PD vary greatly throughout the day. To better understand the diurnal fluctuations of the subject's symptoms, the physician may program a display unit to intermittently alarm over a certain duration of time and to instruct the subject to, for example, wear the sensor on the subject's right hand while performing hand grasping exercises, finger tapping exercises and to simply wear the sensor for a period of time while resting to examine the severity of a subject's rest tremor. The programmed display unit is then sent home with the subject with at least one accompanying sensor and sensor dock. After arrival at home, the subject follows the intermittent instructions provided by the display unit (or records his or her own symptoms according to personal preference if the display unit is not programmed) and then returns the display unit along with its collected data to the physician's office, allowing the physician to then better understand the subject's symptoms and to more effectively treat these symptoms by taking steps to more accurately minimize daily symptom fluctuations.

In still other embodiments, a physician or other clinician may meet with a subject who exhibits symptom's of a movement disorder and, before beginning treatment of the subject, send a programmed movement disorder monitoring device home or to another remote location with the subject where the subject uses the device to record his or her symptoms before returning the device and accompanying data to the physician or other clinician. By examining a subject's symptoms before beginning treatment, a physician or other clinician can establish a "baseline" against which to monitor changes in the severity of a subject's symptoms as treatment methods are changed and/or as time passes and movement disorder symptoms worsen or improve.

It will further be recognized that in certain preferred embodiments, it may be undesirable for a subject to first meet with a physician or other clinician prior to undergoing movement disorder monitoring using the movement disorder monitoring device of the present invention at a remote location. Instead, it may be preferable to directly ship or deliver a movement disorder monitoring device to a subject at a remote location and instruct the subject to return the movement disorder monitoring device upon completion of the assigned monitoring period.

In this way, both the subject and the physician can avoid the cost and inconvenience associated with a preliminary appointment if it is desirable that a symptom baseline first be established for a subject prior to a physician's meeting with the subject or if such monitoring is desired to be conducted to assess, for example, the efficacy of ongoing treatment.

The duration of time during which the movement disorder monitoring device may remain in a subject's home or other remote location with the subject and intermittently provides instructions to the subject and/or allows the subject to "journal" his or her symptoms can vary depending on the nature of the subject's movement disorder and the specific data desired by the programming physician or clinician. In certain preferred embodiments, the movement disorder monitoring device may be in a subject's home for a relatively short period of time such as 8 or even 6 hours. In still other embodiments it may be desirable that the movement disorder monitoring device remain in a subject's home or other remote location for a period of days. In yet other embodiments, it may be preferable to have the movement disorder monitoring device remain in a subject's home for a number of weeks. It will further be appreciated by those of ordinary skill in the art that keeping the movement disorder monitoring device of the present invention in a subject's home for even longer periods of time, such as months or even years, may be desired as a way to better understand a subject's symptoms over a greater duration of time and would provide powerful ways to examine trending in a subject's symptoms over a period of months, years, or even decades.

Certain embodiments of the present invention in which longer movement disorder monitoring times are especially valuable include embodiments in which the movement disorder monitoring device is used to monitor a subject's response to treatment directed at stopping or slowing the onset of a movement disorder. Continuous monitoring over times ranging from months to years to even decades is advantageous with the use of treatment directed at stopping or slowing the onset of a movement disorder because movement disorder symptoms can be very subtle when a movement disorder is in its early stages of development and the objective information provided by the movement disorder monitoring device of the present invention allows a physician or other interested individual to accurately and objectively monitor small changes in symptom severity over time. Thus, by allowing monitoring over a longer period of time, a physician or other clinician or even researcher could use the movement disorder monitoring device of the present invention to collect objective data regarding a subject's disease progression and, hence, the efficacy of a given treatment at stopping or slowing a subject's disease progression. It will further be noted that use of the device and method of the present invention in combination with treatment directed at stopping or slowing the progression or onset of a movement disorder is intended to include use of the movement disorder monitoring device with a broad scope of pharmaceutical agents and/or other treatments directed at stopping or slowing the progression or onset of a movement disorder. Neuroprotective drugs provide one specific example of a compound that can be used to stop or slow the progression or onset of a movement disorder. Briefly stated, neuroprotective drugs include a broad set of compounds that serve to eliminate or reduce neuronal death in the central and/or peripheral nervous systems, hence eliminating certain movement disorder symptoms that can follow neuronal death and stopping progression or onset of a movement disorder disease. By way of specific example, in the case of PD certain drugs have been and are being examined and may be found to be effective at eliminating or reducing death of a subject's dopamine producing neurons, and the efficacy of such drugs over extended periods of time could be objectively monitored using the device and method of the present invention as a means to collect and review movement disorder symptom data over extended periods of time. By way of example, neuroprotective drugs that have been and are being examined for their potential in stopping or slowing the progression of movement disorders such as PD include drugs such as selegiline, riluzole and lazabemide. It is to be understood that the scope of the present invention is intended to cover the use, with the device and as part of the method of the present invention, of these drugs as well as other neuroprotective drugs that may yet be discovered or are currently under investigation.

It will further be appreciated that just as the device and method of the present invention may be used in combination with treatments designed to slow or stop movement disorder onset or progression, the device and method of the present invention may also be used to monitor the efficacy of certain restorative treatments. By restorative treatments it is meant treatments that are directed at restoring the natural function, or close to the natural function, of the part or parts of a subject's body, the failure of which acts as the source of the subject's symptoms. This differs from the other traditional treatments discussed above, such as administration of levodopa to a subject with PD or giving primidone to a subject with essential tremor, in that the goal of a restorative treatment is to eliminate dependence on external treatment of symptoms and instead focus on addressing the source of the problem itself. For example, in many instances such treatment may consist of gene therapy directed at restoring function of certain cells critical to the development and/or symptoms of a subject's movement disorder. In other instances such treatment could consist of implantation of encapsulated cells from an external source, with the encapsulated architecture designed to provide immunoprotection to the encapsulated cells and allow the encapsulated cells to fulfill the role of the subject's native cells that no longer function correctly. By way of specific example, such treatment may comprise the replacement of dopamine producing cells in the substantia nigra region of a subject's brain in a subject diagnosed with PD, using dopamine producing cells encapsulated to prevent a subject's immune response to the implantation. In all of the above, it is to be understood that the scope of the use of the device and method of the present invention in combination with treatments directed at preventing or slowing movement disorder onset or progression or at restoring function of native tissue extends beyond the basic examples provided above and includes all uses and approaches included within the general areas of treatment mentioned.

Various embodiments of the present invention also involve the subject returning the movement disorder monitoring device to a physician's office or another location after use. The method of return can vary depending on a subject's preferences and/or circumstances. In certain instances, the movement disorder monitoring device may be returned in person. In other instances it may be preferable to return the device by mail or courier service. It will be apparent to those of ordinary skill in the art that the movement disorder monitoring device of the present invention is further amenable to return by any other method commonly used to deliver, ship, or transfer items between parties.

Upon return to the physician's or clinician's office or another desired location, the data collected from the subject using the movement disorder monitoring device is preferably transferred from the device to a different location for further analysis and review. Transfer of the data from the movement disorder monitoring device can occur in a number of ways including wireless transfer (e.g. IEEE 802.11 or Bluetooth as mentioned above) from the device, removal of the device memory module and subsequent upload to a separate location, and the use of various data exchange and transfer utilities including the internet or other communication system such as a local area network. Portable data storage devices such as USB flash drives and compact discs can also be used to transfer data from the movement disorder monitoring device for further analysis and review. It will further be noted that it is often the case that combination of the above-noted data transfer methods will be most advantageous.

By way of example, in certain preferred embodiments of the present invention, a USB flash drive may be used to initially transfer data from the display unit of the movement disorder monitoring device. The USB flash drive can then be plugged into a personal computer or other device that has a connection to the internet. The internet connection can then be used to transfer data to a remote database where further analysis and review of data can be performed. In still other preferred embodiments, data transfer may be accomplished by directly connecting the display unit of the movement disorder monitoring device to the internet such as using a WiFi connection or a category 5 data cable connection to allow direct transfer of data form the display unit to a remote database. It will be clear to those of ordinary skill in the art that various other methods beyond the specific examples just provided exist through which movement disorder symptom data can be transferred from a device such as the display unit of the present invention and it is intended that these other methods be included within the scope of the present invention.

As indicated above, various embodiments of the present invention involve the step of further analyzing or reviewing data recorded from a subject as part of a movement disorder monitoring test or series of tests conducted over a period of time. Analysis and review can occur in a number of different ways. In certain preferred embodiments analysis occurs at a remote database where the data is analyzed and processed using certain algorithms to automate the analysis procedure. In other embodiments it may be preferable to upload the data to a remote database so that data may be analyzed by a technician or technically trained clinician as opposed to being automatically analyzed by a processor equipped with algorithms for performing such analysis. In still other embodiments it may be preferable to have the data first automatically analyzed and subsequently checked for accuracy by a technically competent individual. It will further be noted that although analysis in the examples given above occurs after transfer of the data from the display unit of the present invention, data transfer is not always required, and in certain embodiments of the present invention it may be preferable to have the display unit itself perform data analysis, while in other embodiments a personal computer that operates independently from a remote database or other remote facility and is equipped with appropriate software for analysis may be more preferable.

By analysis it is meant that the data is processed to provide a quantitative measurement of a subject's movement disorder testing results. This can be done in a number of ways but generally involves rating the severity of a subject's movement disorder symptoms on some form of scale that allows comparison and/or correlation of a subject's results to certain established standards or to a uniform baseline established by, for example, the treating physician. One example of analysis in this way is the conversion of data obtained from a subject diagnosed with PD using the movement disorder monitoring device of the present invention to produce a result that is correlated with the Unified Parkinson's Disease Rating Scale ("UPDRS"). Correlating the data to match a well-known preexisting standard such as the UPDRS allows a physician to more quickly assess a subject's results and also leads to fewer complications and less training for the physician who adopts the use of the present invention in his or her practice. Data can also be converted to correlate with other known movement disorder scales such as the Hoehn and Yahr scale, the Schwab and England Activities of Daily Living scale, and various general and specific movement disorder severity measurement scales such as those used in assessing essential tremor.

A further part of analyzing the data is to place the data in a format that is easy to read and interpret. This is preferably done by using certain software processes to consolidate the data into a report that uses data tables and graphs or other quickly-understood visual presentations of data. Such presentation of the data allows the individual reviewing the data (e.g. the subject, the physician, or another clinician) to more quickly assess and understand the data. Preferably the data is indexed and displayed relative to time to provide an ordered measure of how the data (or a subject's symptoms) change throughout time. By providing temporal indexing of data in this manner a physician or other individual treating a subject can more accurately adjust treatment method and more efficiently optimize treatment results to ensure a more constant level of treatment efficacy. By way of example of one approach to presentation of data collected using the movement disorder monitoring device of the present invention, in certain embodiments it is preferable that data regarding a subject's movement disorder symptom severity be presented in a two-dimensional table, with time on one axis of the table and movement disorder assessment tasks on the other axis of the table. The spaces in the table are then filled with a value that represents the severity of a subject's movement disorder symptom at a given time and with respect to a given movement disorder assessment task. In certain preferable embodiments, each space in the table may also be color-coded to represent the level of severity of a subject's movement disorder symptoms at any given time for any given assessment task. For example, values that represent severe symptoms my be placed in a red-colored space while values that represent moderate symptoms could be placed in a yellow-colored space and values that represent mild symptoms could be placed in green-colored space. Further, different shades of colors (e.g. different shades of red, yellow and green in the example just given) color could be used to provide even finer color-division among different levels of symptom severity. By color-coding of the table, a physician or other individual viewing the table can more quickly locate areas of trouble for a subject and more quickly and effectively take steps to minimize a subject's movement disorder symptoms. Further, by presenting the data in this way as part of the method of the present invention, the device and method of the present invention may potentially be used in setting a practice-wide standard for objective reporting of movement disorder symptoms.

Regardless of the specific approach or route used in the analysis steps described above, it is preferable in many embodiments of the present invention that a final report be generated that serves to collect and summarize all of the results of the analysis of a subject's movement disorder monitoring conducted using the device and method of the present invention. Preferably, the report may be of varying lengths and the report format and length may be manipulated in certain embodiments by the treating physician or other clinician. Further preferably, the time between starting of movement disorder monitoring data analysis and generation of the final report is less than one day. More preferably this time is less than 6 hours, and still more preferably less than 3 hours. In embodiments in which analysis is conducted automatically by use of a computer and associated algorithms, it is preferable that this time be less than one hour and in certain embodiments less than 5 minutes.

By way of example of the above noted analysis steps, and by way of example of the function of certain software components of the present invention that may be used on a remote server to assist in data analysis, in certain embodiments of the present invention a physician may transfer data from the display unit of the movement disorder monitoring device of the present invention to a portable data storage device and then place this data on a remote server for analysis by a third party. When analysis is complete, the third party may make a report available to the physician who then reviews the report. If the physician has questions or doubts about the report, the physician may watch videos of the subject performing the tests and adjust the report to more accurately reflect the physician's assessment of the subject. When complete, the physician may record his or her impressions or treatment recommendations as part of the report and then print a copy of the report and/or save a copy of the report on the remote sever for later access and subsequent review.

Various embodiments of the present invention include the step of providing the movement disorder monitoring device described herein to a clinician. By providing the movement disorder monitoring device to a clinician, it is meant that the device is provided to a physician, physician's group or location of practice, or any individual employed by, or associated with, a physician's group or practice. A variety of methods exist for providing the movement disorder monitoring device to a clinician. In one form, the movement disorder monitoring device may be provided to a clinician at a reduced price by the device manufacturer and a fee subsequently charged to the clinician for each subsequent use of the device. In other forms the movement disorder monitoring device may be purchased by the clinician or loaned or rented to the clinician under various contractual obligations such as assignment of liability for the device to a certain party and other common contractual stipulations. It will be apparent to those skilled in the art that there are many other methods of providing such a movement disorder monitoring device to a clinician, including various combinations of those methods described above. For example, in one embodiment, the device may be provided to the clinician at a reduced rate; however, liability for loss of, or damage to, the device is placed on the receiving party, or clinician. This is advantageous in that it removes the burden from the movement disorder monitoring device supplier or manufacturer of having to track and maintain devices and carry responsibility for their loss. It also frees the clinician from the burden of paying an overly large up-front fee to purchase the device.

Certain embodiments of the present invention further include the step of charging and collecting fees for use of the movement disorder monitoring device and associated method of the present invention. In certain embodiments, the movement disorder monitoring device manufacturer or device supplier may charge a fee for each time a clinician uses the device to perform movement disorder monitoring of a subject. The clinician, in turn, may also charge the patient a fee for use of the movement disorder monitoring device during the diagnostic procedure. In other embodiments, a clinician may purchase the movement disorder monitoring device of the present invention from the device manufacturer or device supplier without further fees being charged by the manufacturer or supplier. In still other embodiments, a fee may be charged to a first physician who prescribes the movement disorder monitoring test by a second physician or by a technician who interprets and analyzes movement disorder data. In even still other embodiments a fee may be charged to a number of parties (e.g. clinician, subject or both) for the transmission, storage and/or analysis of movement disorder data obtained using the movement disorder monitoring device of the present invention. Still various other methods exist whereby fees may be charged for the use of the device described herein and these methods are intended to be included within the scope of the present invention.

Charging of fees associated with the above-described embodiments can be accomplished electronically or using traditional cash payment methods as well as by installments, or other methods of extending payments over a period of time beyond the time of movement disorder testing. The party to whom the fee is charged in various embodiments of the present invention can be an individual, a group of individuals (including, but not limited to, a physician's practice group), an insurance provider, a third party, or any other entity responsible for payment for services.

Various embodiments of the present invention may involve providing services for transfer, storage and/or analysis of data collected during the course of a movement disorder monitoring study. Preferably, these services are provided by a single entity which controls each step involved in the process. Optionally, these services may be provided by various independent entities working cooperatively to produce the same result as if the steps were controlled by a single entity. Various methods by which data can be transferred, stored and/or analyzed are described above, however, for present purposes it is to be understood that these steps can be performed as part of a method wherein transfer, storage and/or analysis of data are provided for a fee and may be provided as part of a larger process involving the use of the movement disorder monitoring device disclosed herein.

Turning now to a description of the figures, FIG. 1 provides a perspective view of one embodiment of a movement sensor 100 included within the scope of the present invention. The particular embodiment shown in FIG. 1 is designed so as to be worn on a subject's fingertip during use. Accordingly, this embodiment includes a flexible jacket 108 with an elongate opening 110 into which a subject's finger can be placed in order to secure the movement sensor 100 to a subject's fingertip. Preferably the flexible jacket 108 is comprised of a material that is elastically deformable. In this way the elastic forces generated by the material as the material is displaced by the subject's finger allow the sensor to be quickly, but removably, secured to the subject's fingertip. Suitable materials from which the flexible jacket 108 may be constructed include various polymers that can be made to exhibit desired elastic properties such as rubbers, polyolefins (e.g. polyethylene), polyurethanes, silicones, copolymers of these or various other like materials. The embodiment of the movement sensor 100 shown in FIG. 1 also shows a sensor housing 106 that serves to house the electronic and other components of the sensor. These components are discussed in greater detail in the description of FIG. 3 below. In certain preferred embodiments, it is preferable that the sensor's flexible jacket 108 be easily removable from the sensor housing 106. Removability can be accomplished in a number of ways including the use of complimentary geometries on the sensor housing 106 and the flexible jacket 108 that allow the two to easily connect to and be removed from one another, as well as snap-through connections that allow a lower portion of the sensor body to be passed through the flexible jacket 108 and snapped into an upper portion of the sensor body thus securing the sensor body to the flexible jacket. By making the jacket 108 removable, if the flexible jacket 108 becomes worn out, soiled, or otherwise is unsuitable for continued use, the jacket can be easily replaced and the more costly electronic components of the sensor preserved for continued use.

The embodiment of the movement sensor 100 illustrated in FIG. 1 further includes a light emitting diode (LED) 102 that is used as an indicator of the status of the sensor when the sensor is in use. For example, the LED 102 may stay continuously lit when in use, or may flash to indicate that data is being recorded, that a certain amount of time has elapsed, or used to communicate any other simple message that needs to be communicated to the user of the sensor. Also shown in the embodiment of the movement sensor 100 illustrated in FIG. 1 is a point of electronic connection 104, or an input/output port. This electronic connection 104 is used to transfer data to and from the sensor. Also, since the embodiment of the movement sensor 100 shown in FIG. 1 is a wireless embodiment the electronic connection 104 can further be used to supply power to charge the sensor battery (not shown).

It will be noted that while FIG. 1 shows a sensor designed to be worn on the fingertip, other sensors worn on different areas of the body are equally included within the scope of, and amenable for use as part of, the present invention. Such sensors could include wrist-mounted sensors, ring-type sensors worn lower on the finger or sensors on the forearm, feet or other areas at which one might desire to measure movement.

Figure 2:
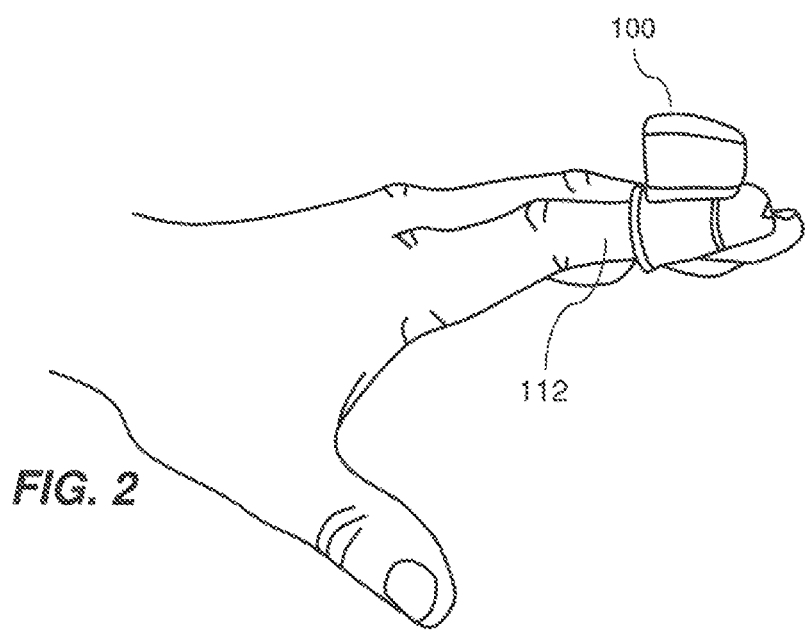
FIG. 2 Perspective drawing of the finger-mounted movement sensor of FIG. 1 as it would be worn when in use.

FIG. 2 is provided as an illustration of the movement sensor 100 of FIG. 1 while in use on a subject's fingertip 112. While FIG. 2 shows the movement sensor 100 being worn on the tip of the left index finger, it will be appreciated that, due to the nature of the flexible jacket 108, the movement sensor 100 could just as easily be worn on any other digit of either of a subject's hands, if such different location is desired. Further, multiple sensors can be used and one or multiple sensors worn on both of a subject's hands if the prescribing physician so desires.

Figure 3:
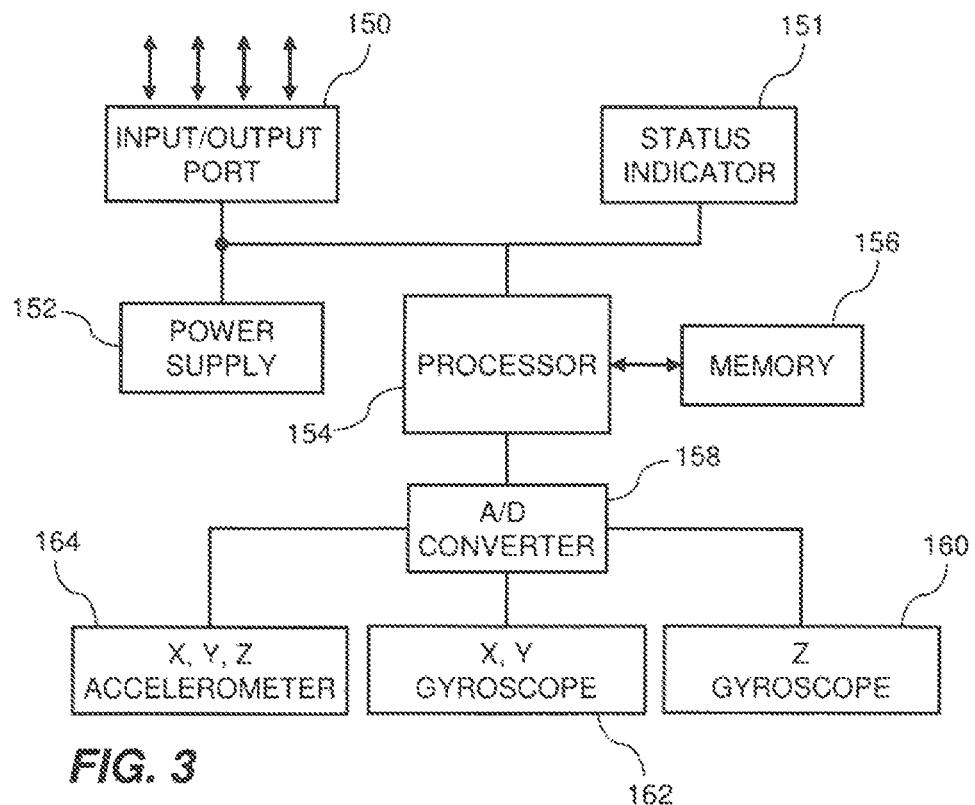
FIG. 3 Block diagram showing interconnection of various component parts of a movement sensor used in various embodiments of the present invention.

FIG. 3 is a block diagram illustrating typical component parts of the movement sensor of the present invention. While the embodiment of the movement sensor 100 shown in FIG. 1 includes these components, various other movement sensors used as part of the present invention also include these components.

Shown in FIG. 3 is a power supply 152 that is used to power the various components of the movement sensor. If the movement sensor is wireless, this power supply 152 could be comprised of a battery, whereas if the movement sensor is instead wired, the supply of power to the sensor could be sourced from a wall outlet, a USB connection to a personal computer, or other power source that typically involves wires as opposed to a battery. If a battery is used it can be of any type commonly known to those of ordinary skill in the art, but is preferably rechargeable such as nickel cadmium, nickel metal hydride, lithium ion, lithium polymer or other like batteries.

The movement sensor further includes an input/output port 150 where data exchange both to and from the movement sensor can take place. In embodiments of the sensor in which the power source is comprised of a battery, the input/output port 150 can also provide a connection to an external source of electricity used to charge the battery. The input/output port 150 connection architecture can take many forms including the various connectors mentioned above such as USB and mini-USB, category 5 data cables, and the like. The input/output port 150 connection could also be a custom-designed connection made specifically for a certain application in which the sensor is to be used or made to specifically mate to a complimentary connection on the sensor dock.

Still further, the movement sensor includes a processor 154 that serves as the central point in handling the acquisition, storage and manipulation or data collected. Among the components illustrated from which the processor collects data are an X, Y, Z accelerometer 164, an X, Y gyroscope 162, and a Z gyroscope 160. X, Y, and Z as used herein refer to the three orthogonal axes commonly used in describing three-dimensional space. In this case, the X, Y, Z accelerometer 164 is able to measure translational movement in all three dimensions while the combination of the X, Y and Z gyroscopes 160, 162 allows rotational measurements in all three dimensions. Thus, use of the sensor allows capturing of movement data with six degrees of freedom and provides a complete measurement of the movement of the extremity to which the sensor is attached. As the accelerometer and gyroscopes are analog instruments it is necessary to covert the signals obtained from these into digital signals before processing and/or storing the signals using the processor 154. To this end, the sensor further includes an analog-to-digital (A/D) converter 158 and a memory 156 for storing the digitized data.

Still further, the movement sensor includes a status indicator 151. The status indicator serves to communicate the status of the sensor to the user. As mentioned above, such a status indicator 151 can be something as simple as an LED like that illustrated in the fingertip-mounted embodiment of the movement sensor 100 of the present invention shown in FIG. 1 or something more sophisticated such as a small liquid crystal display or other more complex indicator.

Figure 4:
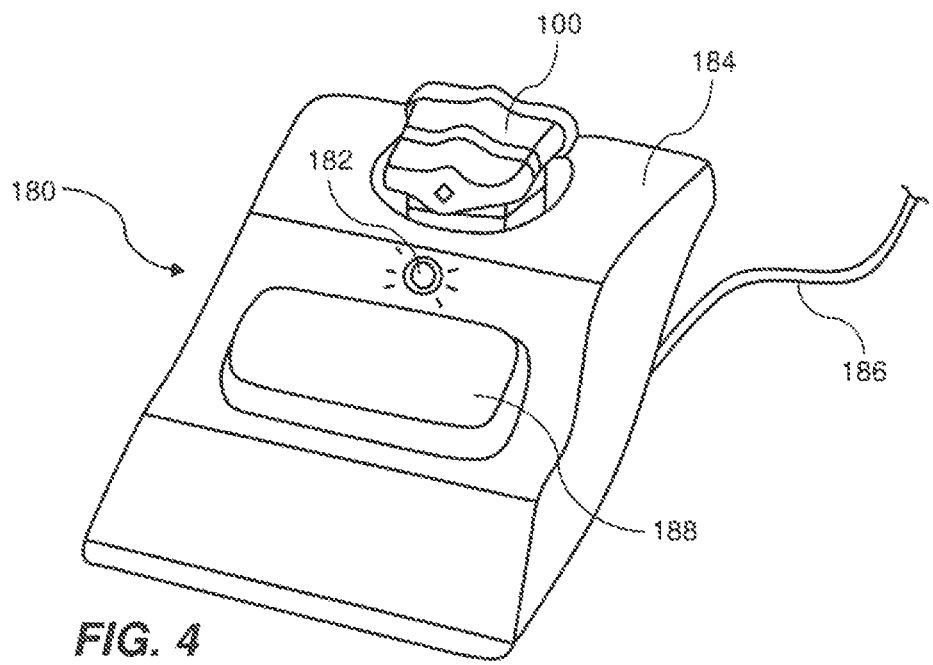
FIG. 4 Perspective drawing of a sensor dock used to store and assist in data transfer when using the movement sensor of FIG. 1.

Referring now to FIG. 4, there is shown one embodiment of the sensor dock 180 of the present invention. The embodiment of the sensor dock shown in FIG. 4 is designed for use with the fingertip-mounted movement sensor 100 of FIG. 1. The sensor dock body 184 is preferably comprised of a rigid material such as a rigid plastic or a thin, rigid metal. As can be seen from the figure, the upper portion of the sensor dock body 184 includes an area for docking of the fingertip-mounted movement sensor 100. As mentioned above, the docking mechanics and design of the dock are preferably such that it is relatively simple for one suffering from a movement disorder to remove and replace the sensor from the dock. In the embodiment of the sensor dock 180 shown in FIG. 4, the sensor is inverted and pressed into the docking area where it makes both a mechanical connection to the dock and an electrical connection to an external device such as a personal computer or the display unit mentioned above and further illustrated in FIG. 5. In this embodiment, connection of the sensor dock to an external device is accomplished using a data transfer cable 186. The cable can be a USB cable, a category 5 cable, or other cable capable of transferring data and/or power to and/or from the sensor in the sensor dock.

The sensor dock 180 further includes a mechanical release button 188 that can be pressed to release the sensor from the dock and that may also optionally serve to sever the electronic connection to the dock. To this end, it is preferred in certain sensor dock 180 embodiments that the movement sensor 100 lock or snap into the dock and subsequently be released upon depression of the mechanical release button 188 or other similar mechanism.

The sensor dock 180 shown in FIG. 4 further includes an indicator 182 that is used to indicate, among other things, whether the sensor has been properly docked. The indicator 182 shown in FIG. 4 is an LED that can be illuminated in response to certain conditions such as the sensor being properly docked, the sensor battery being charged or other conditions that would be important for a user to know. For example, the LED could illuminate in certain patterns to communicate to the user certain states. It will be clear to those of ordinary skill in the art that still other indicators could be used such as multiple LEDs of various colors or a small liquid crystal display or other similar dynamic display if desired.

It will be noted that FIG. 4 is illustrative of only one embodiment of the sensor dock of the present invention and other embodiments could include sensor docks of still different forms such as a dock that connects wirelessly to external devices or a dock that can accommodate more than one sensor, and other like changes that fall within the scope of the disclosure included herein.

Figure 5:
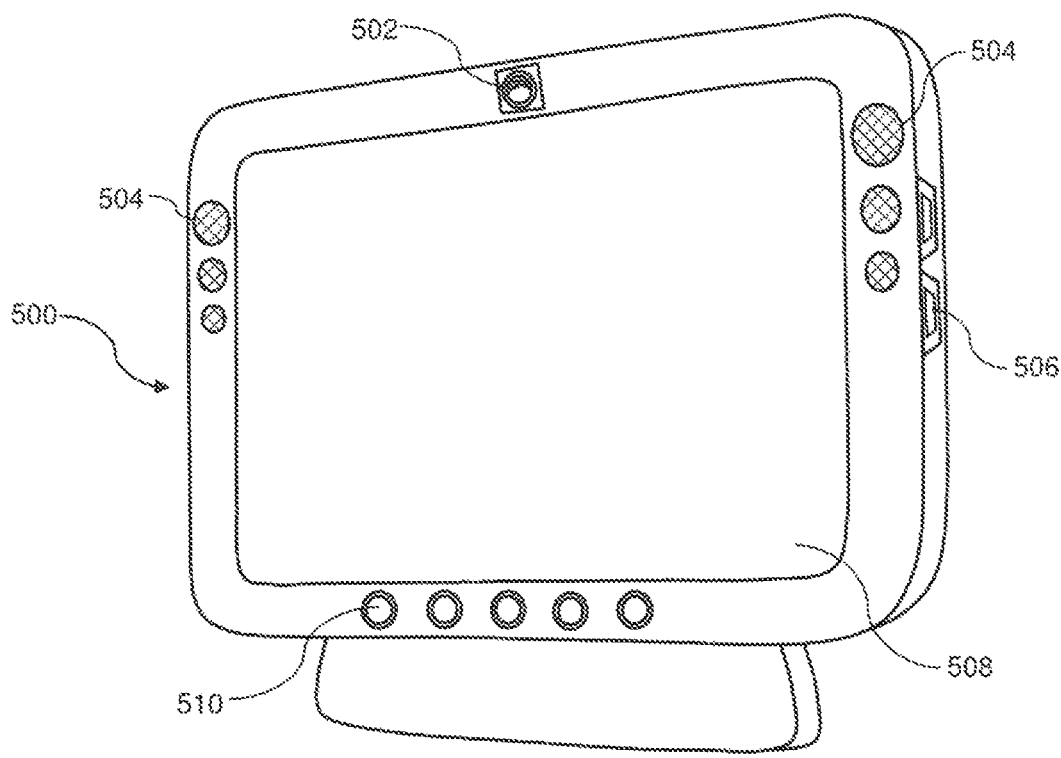
FIG. 5 Perspective drawing of a display unit used in certain embodiments of the present invention.

Turning now to FIG. 5, there is shown one embodiment of the display unit 500 of the present invention. As noted above, the display unit is generally programmed by a physician or clinician to perform certain functions or provide certain instructions to a subject at various desired points in time over a desired duration of time. The embodiment of the display unit 500 shown in FIG. 5 includes a display screen 508. Preferably this screen is a touch-sensitive liquid crystal display that allows a subject or physician to input data by either touching the screen in a desired area with a finger or through the use of a stylus that is designed to function with the screen.

The display unit 500 further includes audio speakers 504, a camera 502, and input/output ports 506. The audio speakers 504 of the display unit 500 are preferably be used to communicate audio information that accompanies information displayed on the display screen 508. Such audio information could be verbal instructions that accompany a demonstration video or could be instructions on how next to proceed with data input or any other instructions that may be beneficial or necessary to the user of the present invention. The camera 502 of the display unit can be used to photograph or video record a subject while the subject executes the instructions provided by the display unit. This recorded video or photograph data can then be stored and recalled at a later point in time to ensure a subject's compliance with movement disorder testing instructions received from the display unit 500. The input/output ports 506 of the display unit 500 are used both to send and receive data to and from the display unit. The input/output ports 506 shown can take a number of forms including, by way of example, USB, mini-USB and category 5 cable and could further just as easily consist of an optical drive for reading data from a compact disk or other optically-readable media. In addition to those items just discussed, although not shown in the embodiment of FIG. 5, the display unit may also optionally include a microphone for recording audio from a user in addition to video or photographs recorded by the camera.

The display unit can be adjusted using input and adjustment buttons 512 located below the display screen 508. The adjustments that may be made using the adjustment buttons include toggling of the camera on and off, adjustment of speaker volume, display brightness, or other similar desired functions. It will be clear to those of ordinary skill in the art that such input and adjustment buttons 512 may not always be needed since in other embodiments one could program the software to perform such functions in response to input received through the touch-sensitive display screen 508, thus eliminating the need for external buttons to provide such input.

It will be noted that the embodiment of the display unit 500 shown in FIG. 5 is only one example of the form the display unit of the present invention may take and there are many other forms that may be used with various different features including simply using a standard portable personal computer.

Figure 6:
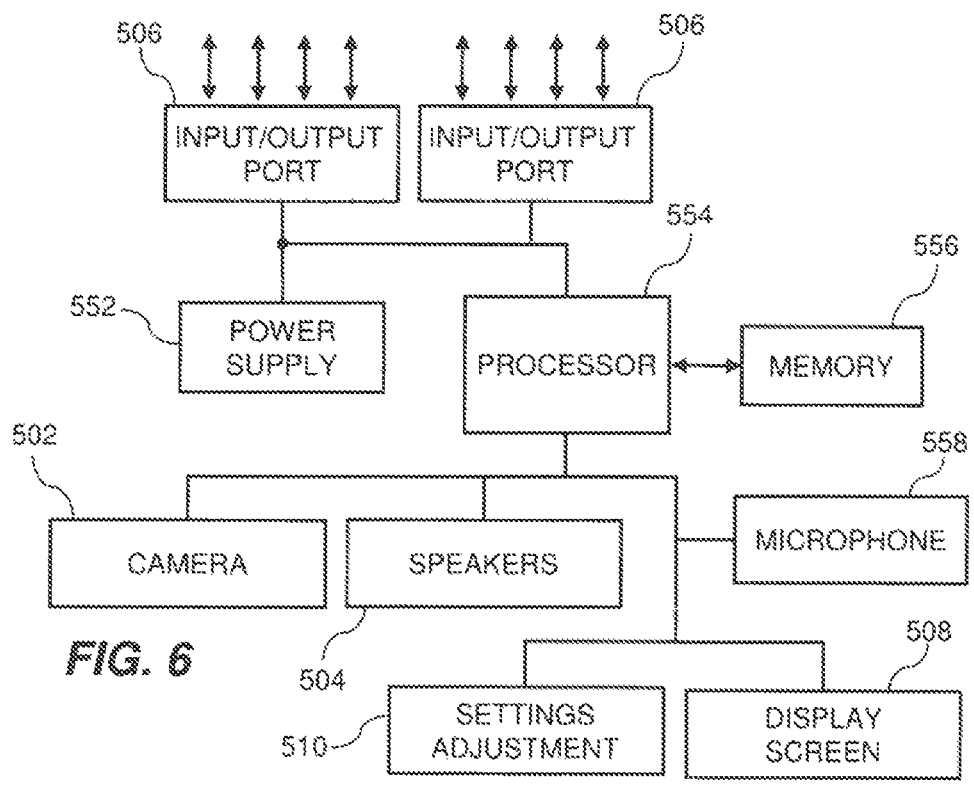
FIG. 6 Block diagram showing interconnection of various component parts of a display unit used in various preferred embodiments of the present invention.

FIG. 6 shows a simplified block diagram illustrating typical parts of the display unit of the present invention. While the specific embodiment of the display unit 500 shown in FIG. 5 includes these components, various other embodiments of the display unit of the present invention may also include these or other components and it is to be understood that the block diagram of FIG. 6 is representative of a greater variety of embodiments of the display unit than the single example provided in FIG. 5.

It will be noted that many of the components shown in FIG. 6 have already been addressed in the above description of FIG. 5. The components already discussed include the input/output ports 506, the camera 502, the audio speakers 504, the settings adjustment buttons 510 and the display screen 508. All of these components are powered by the display unit power supply 552. In certain embodiments, the display unit power supply 552 can be a battery. If a battery is used it can be of any type commonly known to those of ordinary skill in the art, but is preferably a rechargeable battery such as nickel cadmium, nickel metal hydride, lithium ion, lithium polymer or other rechargeable batteries. In other embodiments it is preferred that the display unit power supply 552 be a wired connection to an external power source such as, for example, a connection to a standard 120-volt outlet or other household outlet. In still other embodiments it is envisioned that the display unit power supply 552 will be a combination of both a battery as well as other external power sources.

The display unit processor 554 is connected to the display unit memory 556 and is thus able to serve to coordinate input and output from both internal components and external devices and store data when needed.

Further shown in FIG. 6 is a microphone 558 connected to the processor 554. In certain embodiments it is preferable to have a microphone as part of the display unit as this allows a subject's voice to be recorded for later listening or for a subject's voice to be heard at in real-time at a remote location such as if the display unit were to be connected to the internet in such a way as to allow real-time data transfer to a remote location. It will be noted that recording of a subject's voice can be significant in monitoring of certain movement disorders as there are a number of movement disorders that involve quavering, or tremor, of the voice, such as essential tremor.

Figure 7:
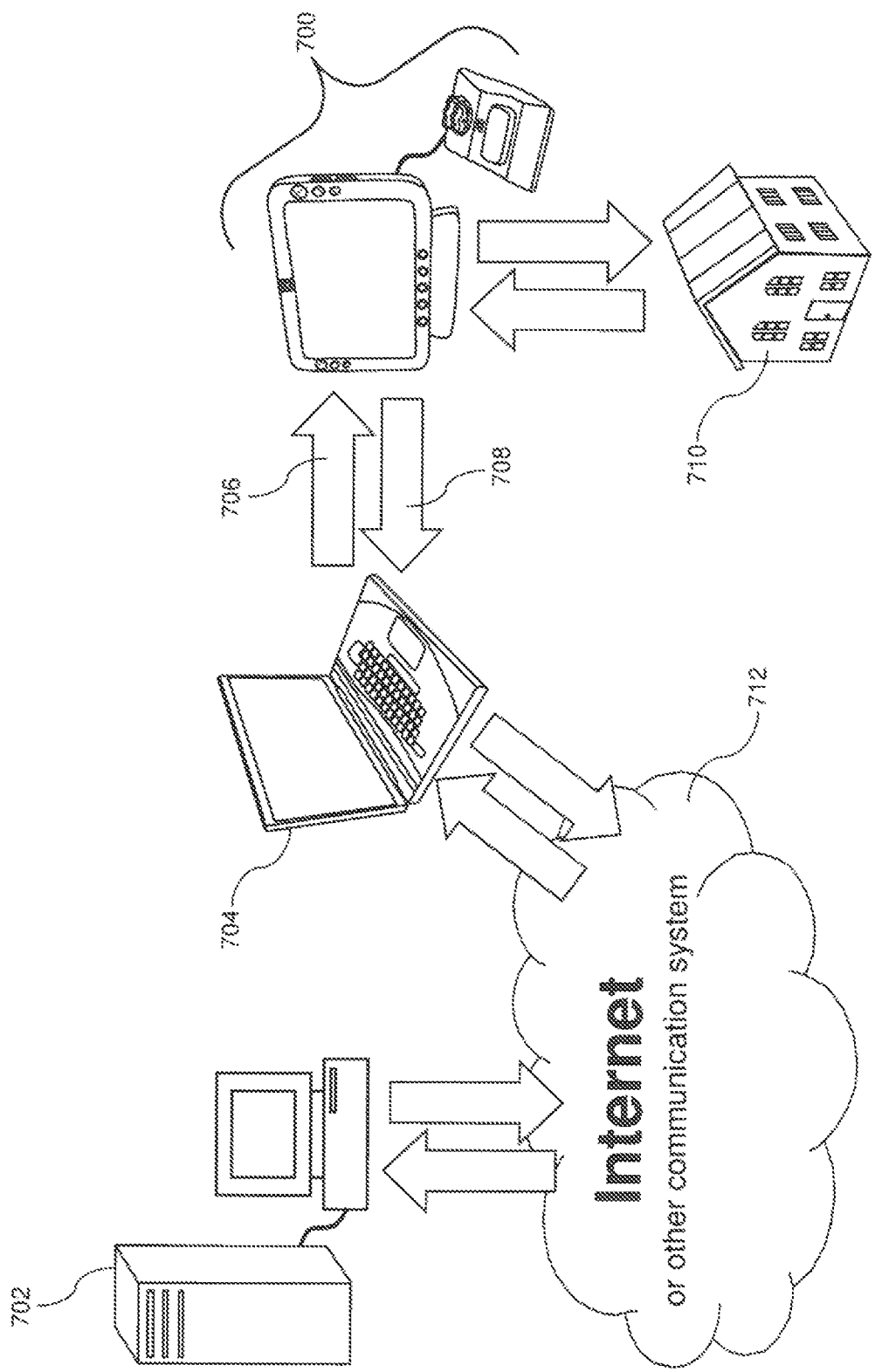
FIG. 7 Schematic representation of both the interrelation of various components of the present invention and an accompanying method of use of the various components.

Turning now to FIG. 7 there is shown a schematic diagram of one preferred embodiment of the present invention illustrating the various parts of the invention disclosed herein and the steps involved in using the invention. In the embodiment of FIG. 7 a physician or other qualified clinician first meets with a subject and determines that a remote monitoring study of the subject's movement disorder symptoms is advisable. The physician or clinician then uses a personal computer 704 connected to the internet or other communication system 712 to access a remote database and its accompanying website 702. When the physician or other clinician arrives at the website, he or she logs into a previously established account, initiates a new study by inputting information about a subject (e.g. age, symptoms, diagnosis and the like), and uses software from the remote database 702 presented through a web browser to set specific parameters desired for the remote monitoring study of the subject's movement disorder symptoms. Examples of the parameters available to the physician for selection and execution during the remote monitoring procedure include the duration of the procedure, specific tasks required of the subject during the procedure, the frequency of tasks required of the subject and requiring the subject to input his or her subjective assessment of symptom severity. It will be clear to those of ordinary skill in the art that there are many other parameters could be made available for selection by a physician and those other parameters not included in the example above are nevertheless intended to be included in the scope of the present invention.

When information about a subject has been entered and study parameters selected, the physician or other clinician is then allowed to download a file from the remote database that includes the parameters of the study and other information and that is subsequently loaded 706 onto the movement disorder monitoring device 700 of the present invention. Loading of the file 706 onto the movement disorder monitoring device 700 can be accomplished in a number of ways, but in certain preferred embodiments is accomplished by saving the file to a USB flash drive and using the USB flash drive to transfer the file to the display unit of the movement disorder monitoring device 700. Preferably, the saved file is a self-executing file that is recognized by the display unit software and automatically loaded upon docking of the USB flash drive.

Once the file is loaded onto the display unit of the remote movement disorder monitoring device 700, the device is sent with the subject to, for example, the subject's home 720 where the display unit software will intermittently cause the display unit to alarm and subsequently provide instructions to the subject to place the movement sensor of the remote movement disorder monitoring device on the subject's finger and perform certain movement disorder measurement tasks selected by the prescribing physician or other clinician that allow quantification of the severity of a subject's movement disorder symptoms. The software may also instruct the subject to enter data concerning the subject's personal assessment of his or her symptom's as well as the steps taken by the subject to alleviate movement disorder symptoms such as the dosage of a certain drug and the time at which the dose was administered.

After all data is collected over the period of time specified by the physician or clinician, the subject returns the remote movement disorder monitoring device 700 to the physician or clinician. Upon return of the movement disorder monitoring device 700, the physician or clinician extracts 708 the recorded data from the device and uses a personal computer 704 connected to the internet or other communication system 712 to transfer the data to the remote database 702 for further analysis and review. Extracting or downloading 708 the recorded data from the movement disorder monitoring device 700 can be accomplished using any of the data transfer methods mentioned herein, however, in certain embodiments it is preferred that the data be transferred using a USB flash drive that is first docked with the display unit of the movement disorder monitoring device 700 and used to record the movement disorder measurement data and is then docked with the personal computer 704 where the internet or other communication system 712 is used to transfer the data to a remote database 702.

At the remote database, the data obtained from the remote monitoring study of the subject's movement disorder symptoms can be either manually or automatically analyzed and a report subsequently generated and securely made accessible to the physician or other clinician via his or her respective account. The physician or other clinician can then use this report to gain greater insights in a subject's movement disorder symptom severity as well as to more efficiently optimize a subject's treatment regimen.

As already noted above, it is preferred that all data transfer involved in the embodiment shown in FIG. 7 is preferably accomplished in a secure and private way whether through the use of direct secure connections, data encryption or other similar methods known to provide secure avenues for data sharing.

Figure 8A:
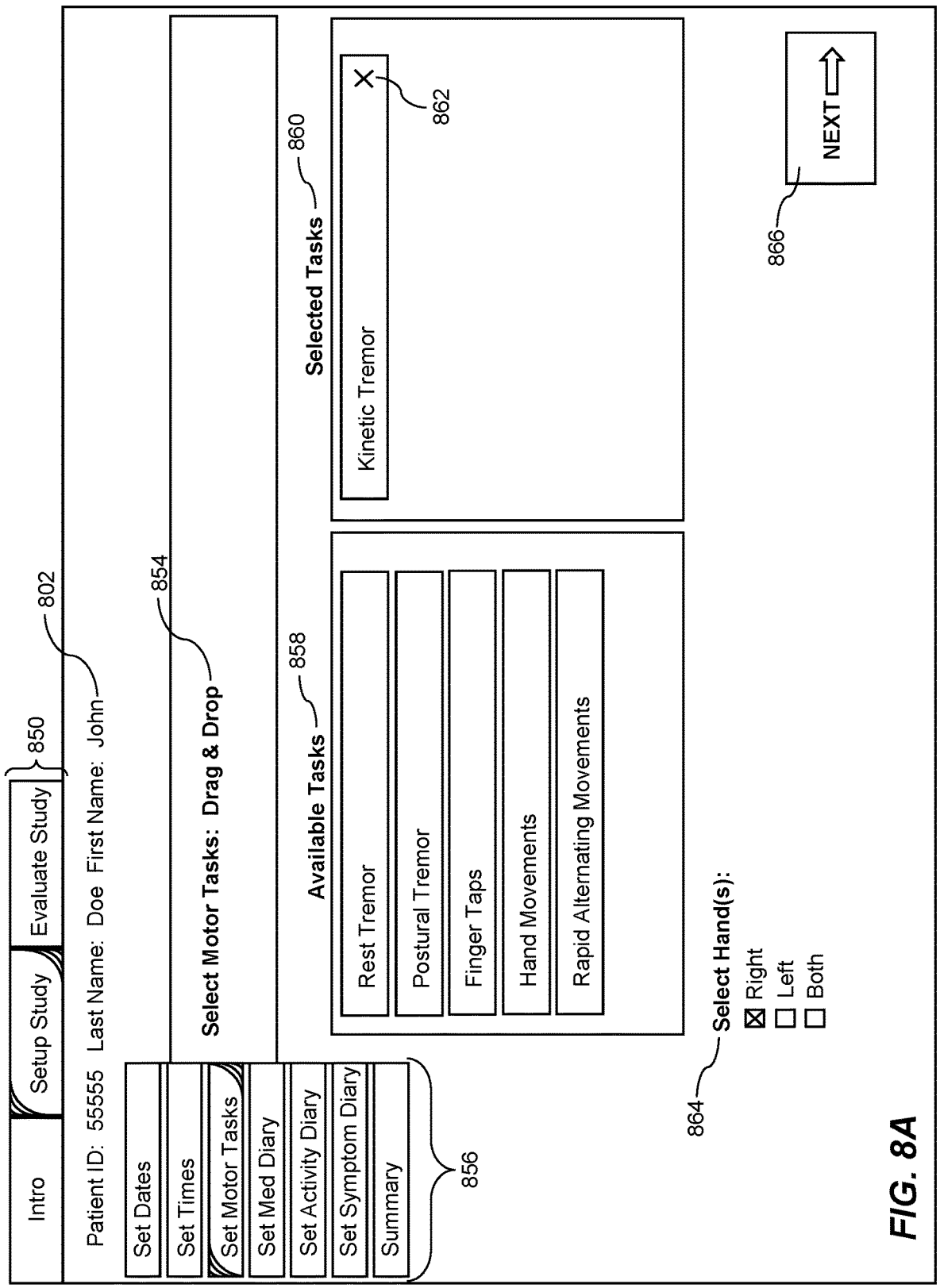

Turning now to FIG. 8A there is shown one embodiment of the software interface of the present invention that may be used by a physician or other clinician in programming the display unit of the movement disorder monitoring device of the present invention. The software interface of FIG. 8A may be made available to a physician either through a web browser using the internet or other communication system 712 and software located on the remote database 702 of FIG. 7 or by installing the actual software on a physician's personal computer. It will be noted that FIG. 8A shows only one selection from a number of software options available as part of an overall larger software application. Specifically, FIG. 8A illustrates what might be displayed when the "Set Motor Tasks" submenu is selected from under the "Setup Study" menu. As illustrated in FIG. 8A, however, there are a number of different menus 850 available to a physician including an introduction to using the software and a menu that allows a physician or other clinician to evaluate a completed in-home movement disorder study. Each of the available menus 850 may also have a number of submenus 856 that allow a physician or other clinician to adjust or examine more specific options associated with a given submenu selection. In FIG. 8A it can further be seen that the various submenus 856 available under the "Setup Study" menu allow a physician or other clinician to select from a variety of options in order to customize any given movement disorder study to meet the physician's desired parameters of, for example, duration, recording of medication regimens, and recording of indicators of a subject's activity levels.

Turning now to the specific example illustrated in FIG. 8A, it can be seen that the data displayed includes subject identification data 802 that includes a subject's name and may also include a unique ID number assigned to the subject. Among the options available to a programming physician or other clinician in the "Set Motor Tasks" submenu of the "Setup Study" menu, the physician or other clinician may select from a list of available movement disorder assessment tasks that can be programmed for a subject to perform during a remote movement disorder monitoring study. By following the instructions 854 to drag desired available tasks 858 to the "Selected Tasks" box 860 the motor tasks desired for a given study can be customized to that study. Once a task has been moved to the selected tasks box 860 it can be removed from the selected tasks box 860, if desired, by selecting the removal function 862. In the embodiment of FIG. 8A the software is designed to be used with a movement sensor worn on a subject's hand or finger(s). Accordingly, the programming physician or other clinician can use the software interface to select which hand, or both, on which the subject is to wear the movement sensor(s) of the present invention 864. When setting of motor tasks is complete the programming physician or other clinician may select the "Next" button 866 to move to the next programming step.

In FIG. 8B there is shown a portion one embodiment of a report that may be generated and made available to a physician either through a web browser using the internet or other communication system 712 and software located on the remote database 702 of FIG. 7 or by installing the actual software on a physician's personal computer. It will be noted that the data illustrated in the embodiment of FIG. 8B shows only one selection from a number of report viewing options available as part of an overall larger software application. Specifically, FIG. 8B illustrates what might be displayed when the "Motor Trends" submenu is selected from under the "Evaluate Study" menu. As illustrated in FIG. 8B, however, there are a number of different menus 800 available to a physician including an introduction to using the software and a menu that allows a physician or other clinician to set up a new study for a subject. Each of the available menus 800 may also have a number of submenus 806 that allow a physician or other clinician to adjust or examine more specific options associated with a given submenu selection. In FIG. 8B it can further be seen that the various submenus 806 available under the "Evaluate Study" menu allow a physician or other clinician to examine such things as the subject's assessment of his or her symptoms (i.e. under the "Diary Trends" menu) or to create a custom report for printing or saving that captures the specific data desired by the physician or other clinician.

Turning now to the specific example illustrated in FIG. 8B, it can be seen that the data displayed includes subject identification data 802 that includes a subject's name and may also include a unique ID number assigned to the subject. Among the options available to a reviewing physician or other clinician in the "Motor Trends" submenu of the "Evaluate Study" menu, the physician or other clinician may choose to view a plot 810 of movement disorder symptom severity as it is tracked over time. The example plot shown in this specific embodiment shows data collected regarding rest tremor severity of a subject's left hand. It will be noted that different symptoms can be illustrated at the same time using differently colored or differently shaded plot columns to distinguish between different symptoms. For example, certain columns may be shaded differently to represent a subject's exhibiting bradykinesia 818 and the severity of the subject's bradykinesia, while another column or columns may be left unshaded or shaded with a different color to represent the severity of a subject's rest tremor 816. Still other data may be included on the plot 810 such as the time point at which a subject took or was administered a dose of drug 812 intended to alleviate the subject's movement disorder symptoms.

A matrix or table 814 may also be displayed as a means to provide a physician or other clinician a deeper understanding of how a subject's movement disorder symptoms fluctuate throughout the day. The table 814 shown in FIG. 8B displays data recorded at different times while a subject performed certain movement disorder assessment tasks. The specific tasks displayed as part of the table 814 can be modulated by the physician or other clinician by selecting the desired display options 804 from the submenu interface above the table.

Further illustrated in FIG. 8B is the capability that, if a subject has had a number of remote monitoring studies performed, the physician or other clinician may view data from different dates on which the studies were performed 808. By allowing the physician or other clinician to view studies conducted on different dates over varying lengths of time, he or she will be better able to monitor progression of a subject's symptoms over time and will be able to objectively review trending in the subject's symptoms over extended periods of time. The table 814 itself provides a tabular view of how a subject's movement disorder symptoms fluctuate over time relative to specific movement disorder assessment tasks. The number located in any given space in the table is a measure of the subject's ability to execute a specific activity at a specific time during the day. In this instance the numbers happen to be correlated to UPDRS scores and range on a scale from 0 to 4, but these numbers could just as easily be displayed in terms of other assessment scales used in evaluation of movement disorder symptom severity. In certain embodiments, it is preferable that each space in the table 814 be color coded to reflect the severity of a subject's symptoms based on the number or value located in the space. For example, in the table 814 shown in FIG. 8*b* it is preferable that the space surrounding higher numbers be colored red, the space surrounding moderate numbers be colored yellow, and the space surrounding low numbers be colored green. Various shades of colors or more than three colors may also be used to provide finer resolution to the color coding used in the table 814. By color coding the data included in the table 814 a physician or other clinician assigned to review the data in the table can quickly isolate the movement disorder assessment tasks that give the subject the most difficulty and at what times the subject has the most difficulty completing assessment tasks. In this way, treatment of a subject's symptoms can be more quickly optimized and reading of the data can be made more efficient. It will further be noted that table 814 also shows the mean score for a subject's symptom severity throughout the timepoints examined as well as the level of fluctuation in symptoms that occurred throughout the timepoints examined. Such data further assists a physician in efficiently and effectively identifying problem areas for a subject and taking appropriate steps to ameliorate a subject's symptoms.

Figure 9:
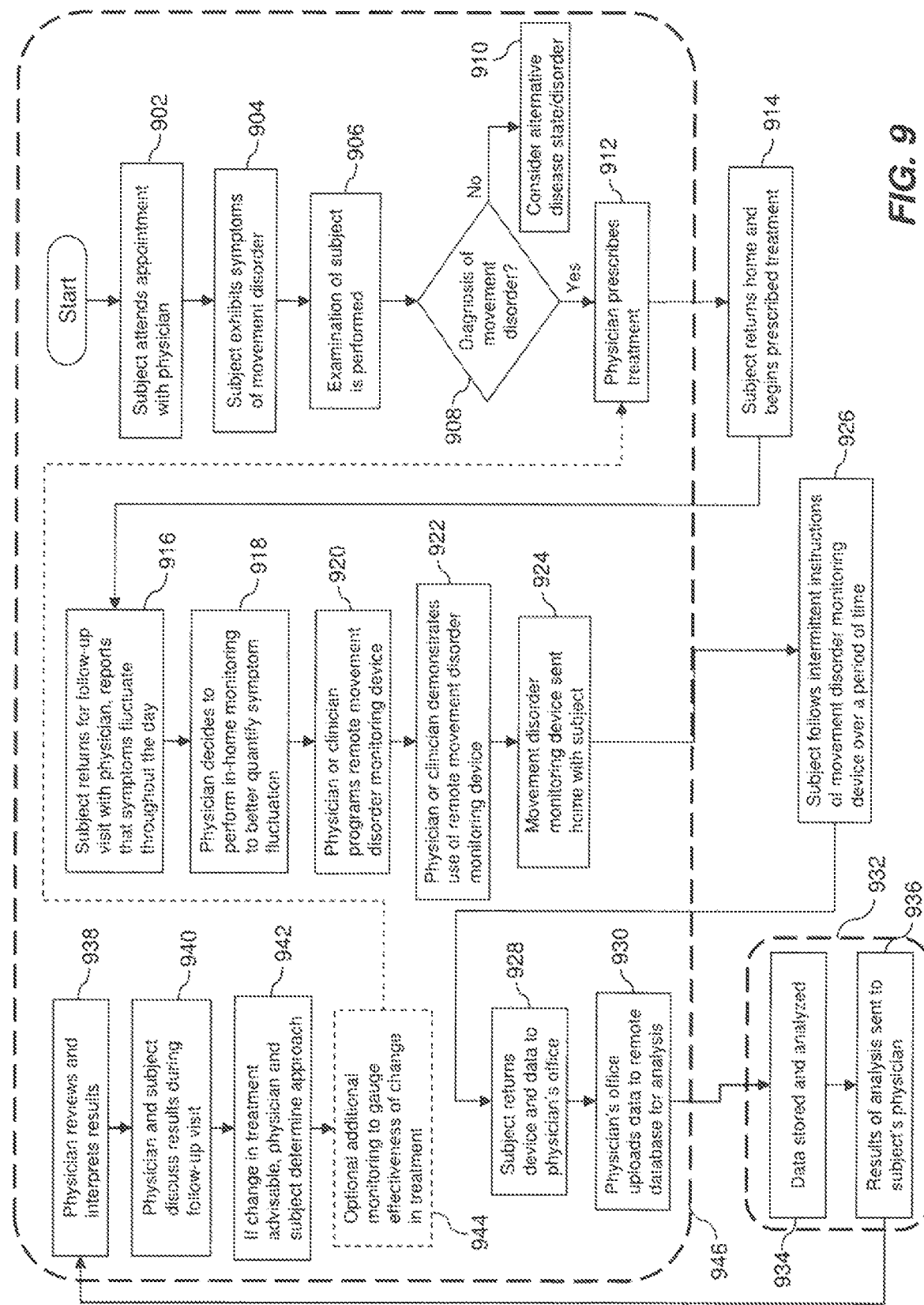
FIG. 9 A flow chart illustrating one embodiment of a method of use of the device of the present invention in a clinical setting.

FIG. 9 is a flow diagram that illustrates one embodiment of a method of use of the device of the present invention in a clinical setting. In discussing FIG. 9, it will be noted that box 946 represents a physician's practice or place of business. For purposes of this figure, steps occurring within box 946 represent steps that occur within the physician's office or place of practice and that are performed by the physician or another capable individual associated with the physician's practice. It will further be noted that box 932 represents a remote processing and analysis station. Accordingly, steps that occur within box 932 occur at a site remote from the physician's practice or place of business such as the location of a remote database or the location of a technician trained to read movement disorder study data. Boxes 926 and 914 represent steps taken by a subject at a location remote from both the remote processing and analysis station 932 as well as the physician's practice or place of business 946. Examples of such a location include a subject's home or a long-term care facility.

The method depicted in FIG. 9 includes the first step of having subject attend an appointment with a physician or other clinician 902. If during the appointment with the physician or other clinician it is determined that a subject exhibits symptoms of a movement disorder 904 a more in-depth examination of the subject is performed 906 so that an accurate diagnosis can be reached. If the diagnosis 908 is that the subject does not suffer from a movement disorder the physician may then proceed to consider an alternative disease state. However, if the diagnosis 908 is that the subject does, in fact, suffer from a movement disorder then the physician preferably prescribes some form of treatment to the subject 912. Such treatment can include physical therapy or exercise regimens, pharmaceutical or drug based treatment or other movement disorder treatments that will be known to those of ordinary skill in the art such as electrical stimulation therapies. After prescription of treatment the subject then leaves the physician's place of business and returns home or to some other location to begin the prescribed treatment 914. Depending on the nature of the prescribed treatment various amounts of time may be allowed to pass before the subject returns to the physician's office for a follow-up visit 916. For example, if drug-based treatment is prescribed it may be desirable to allow 15 to 30 days to pass before a follow-up visit is conducted to allow time for the subject's body to adjust to the effects of the drug and to allow the drug time to have the desired affect.

In the embodiment of FIG. 9 the subject reports at the follow-up visit 916 that he or she experiences noticeable fluctuations in movement disorder symptom severity throughout the day. It will be noted that at this step the method illustrated in FIG. 9 is also easily adaptable for use with individuals who have previously been diagnosed with a movement disorder and whose ongoing therapy fails to minimize daily symptom fluctuation. As a way to gain greater insight into the level and timing of symptom fluctuation experienced by the subject, the physician in this case chooses to conduct a remote movement disorder monitoring study in the subject's home 918 using the movement disorder monitoring device of the present invention. Accordingly, the physician programs a remote movement disorder monitoring device 920 using processes and techniques already discussed herein. After a demonstration to the subject on proper use of the movement disorder monitoring device 922 the physician then sends the movement disorder monitoring device home with the subject 924 for an appropriate period of time determined by the physician. As mentioned above, the period of time during which the movement disorder monitoring device remains with the subject in his or her home can range from hours to years depending upon the duration deemed appropriate by the prescribing physician. The duration is set by the physician during the step of programming.

Upon arriving home, the subject follows the intermittent instructions received from the display unit of the movement disorder monitoring device of the present invention 926. As the subject follows the instructions and uses the sensor of the present invention, data is collected and stored regarding the severity of the subject's movement disorder symptoms at various times throughout the study period.

At the conclusion of the study period, the subject returns the movement disorder monitoring device, with the accompanying recorded data to the physician's place of business 928. By way of example, the subject may return the movement disorder monitoring device by prepaid expedited courier service paid for by the physician's practice or by the subject themselves. Upon receipt of the movement disorder monitoring device and the recorded data, the physician uploads the data 930 to a remote database for further processing and analysis. The data is then stored on the database and analysis conducted 934 at a remote site. As mentioned elsewhere herein, analysis can be conducted automatically with software-based algorithms, manually by a trained technician, or a combination of automatic and manual analysis. Once analysis is complete a report is generated and the results are sent or made available for review by the prescribing physician 936. For example, the report could be made accessible to the physician via a controlled-access world wide web portal. In other embodiments this step may further include sending of a paper copy of the results to a physician's place of business.

After reviewing the results of the remote movement disorder monitoring study 938 the physician again sees the subject for a second follow-up appointment 940 during which the results of the study are discussed. If it is determined that change in treatment approach is advisable such change is adapted and implemented 942 as part of this second follow-up visit. By way of example, such a change in treatment may consist of a change in the frequency and/or volume of drug dosages. A further example could include changing of the stimulation parameters of a deep brain stimulation device for a subject being treated with deep brain stimulation.

As a final step in the method depicted in FIG. 9, an optional follow-on remote movement disorder study may be conducted 944 to assess the effectiveness of changes in treatment by repeating certain steps of the method after a change in treatment has been adopted.

Figure 10:
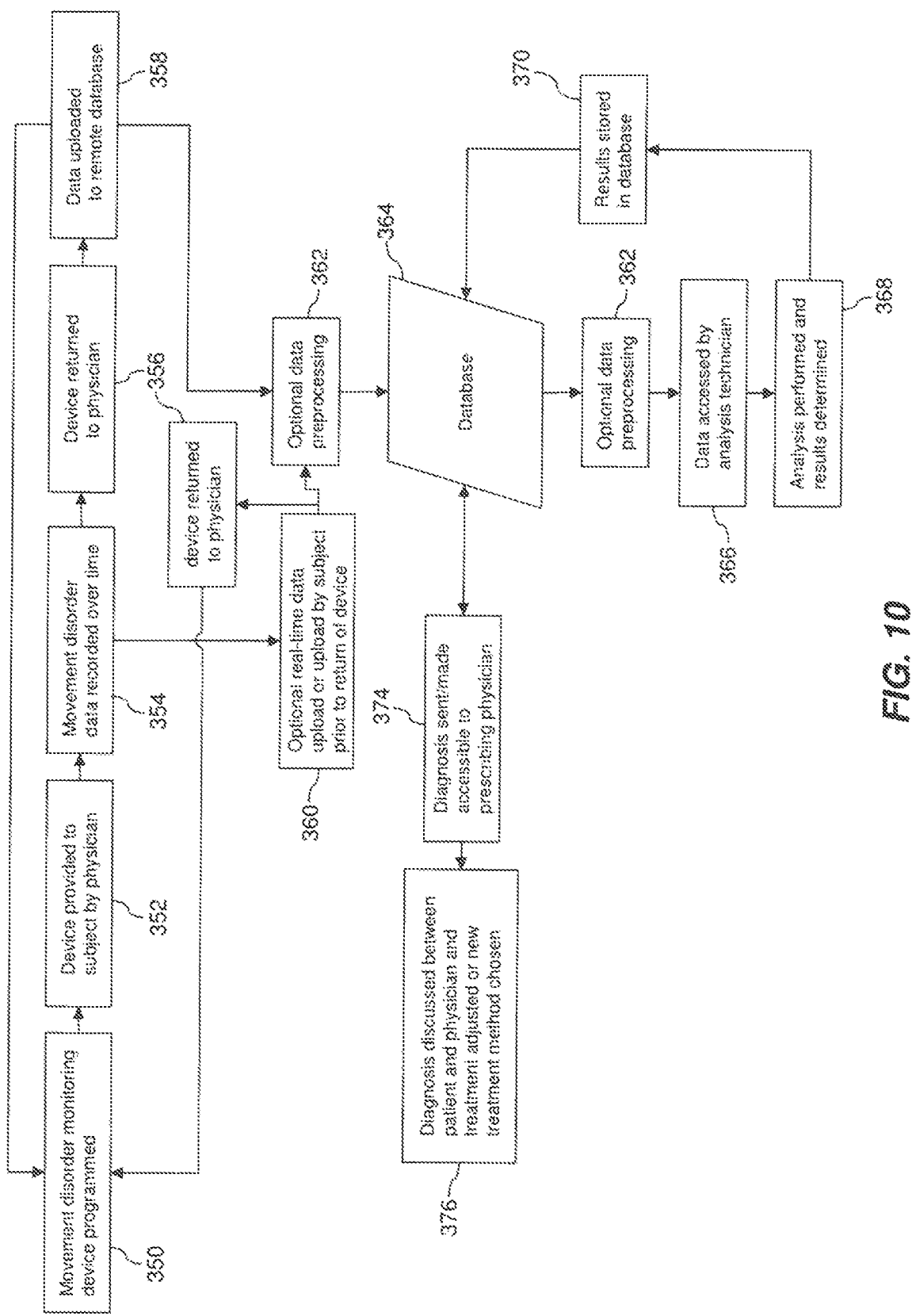
FIG. 10 A flow chart illustrating the flow of data collected from a remote movement disorder monitoring study conducted using the device and method of the present invention.

Turning now to FIG. 10, there is shown a flow diagram illustrating the flow of data collected for certain embodiments of the present invention during a remote movement disorder monitoring study. In the first step depicted in FIG. 10 the movement disorder monitoring device is programmed 350 by a physician or other clinician using techniques previously discussed herein. As before, the movement disorder monitoring device is sent with the subject 352 after programming and the subject then takes the device to a remote location where data about a subject's movement disorder symptom severity is collected from the subject 354 as the subject follows the instructions provided by the movement disorder monitoring device and properly uses the sensor or sensors of the movement disorder monitoring device disclosed herein. The movement disorder monitoring device, now containing data pertaining to the variance and severity of a subject's movement disorder symptoms, is then returned by subject to the physician or physician's office 356 using any of the methods that have been previously discussed herein. Upon return of the device, the data collected using the movement disorder monitoring device is uploaded 358 to a database 364 for future analysis. Optionally, movement disorder monitoring device data can be uploaded to a database 364 in real-time or near real-time 360 as data is collected from a subject using, for example, a secure internet connection from a subject's home to the appropriate remote database. Further optionally, the subject themselves could upload the movement disorder monitoring device data to a database 364 at the completion of all movement disorder assessment tasks, but prior to return of the device to the physician or physician's office, using a household internet connection or other similar means.

In certain preferable embodiments of the present invention, movement disorder monitoring device data is preprocessed 362 prior to manual analysis and review by a technician or even prior to automatic analysis using certain software algorithms. As shown in FIG. 10, the step of preprocessing 362 can be performed either before or after storage of the movement disorder monitoring device data in a database 364, but prior to analysis of the data. Preprocessing can involve a number of approaches to examining and manipulating data before final analysis, but most preferably involves screening the data to ensure that all data are in line with rational expectations and that the data has not been corrupted or otherwise rendered unreadable or misformatted in some way. After storage in the database 364 and optional preprocessing of the data 362, the data collected using the movement disorder monitoring device may be accessed by a technician 366 assigned to analyze the data and an analysis conducted and results determined 368. Alternatively, though not depicted in FIG. 10, the data could instead be automatically processed using a software application designed for such purpose. The results of the data analysis are then stored 370 in the database 364 and made accessible to the prescribing physician 374 by providing access to digital copies of the results stored in the database, through the mailing of hard copies of the results to the physician or a combination of these or other methods for providing information to individuals. Upon receipt of the movement disorder study analysis and results by the prescribing physician, the subject is provided access to the results through a follow-up appointment with the prescribing physician 376. Preferably this step includes not only a discussion of results but also discussion of possible changes in treatment where necessary.

Figure 11:
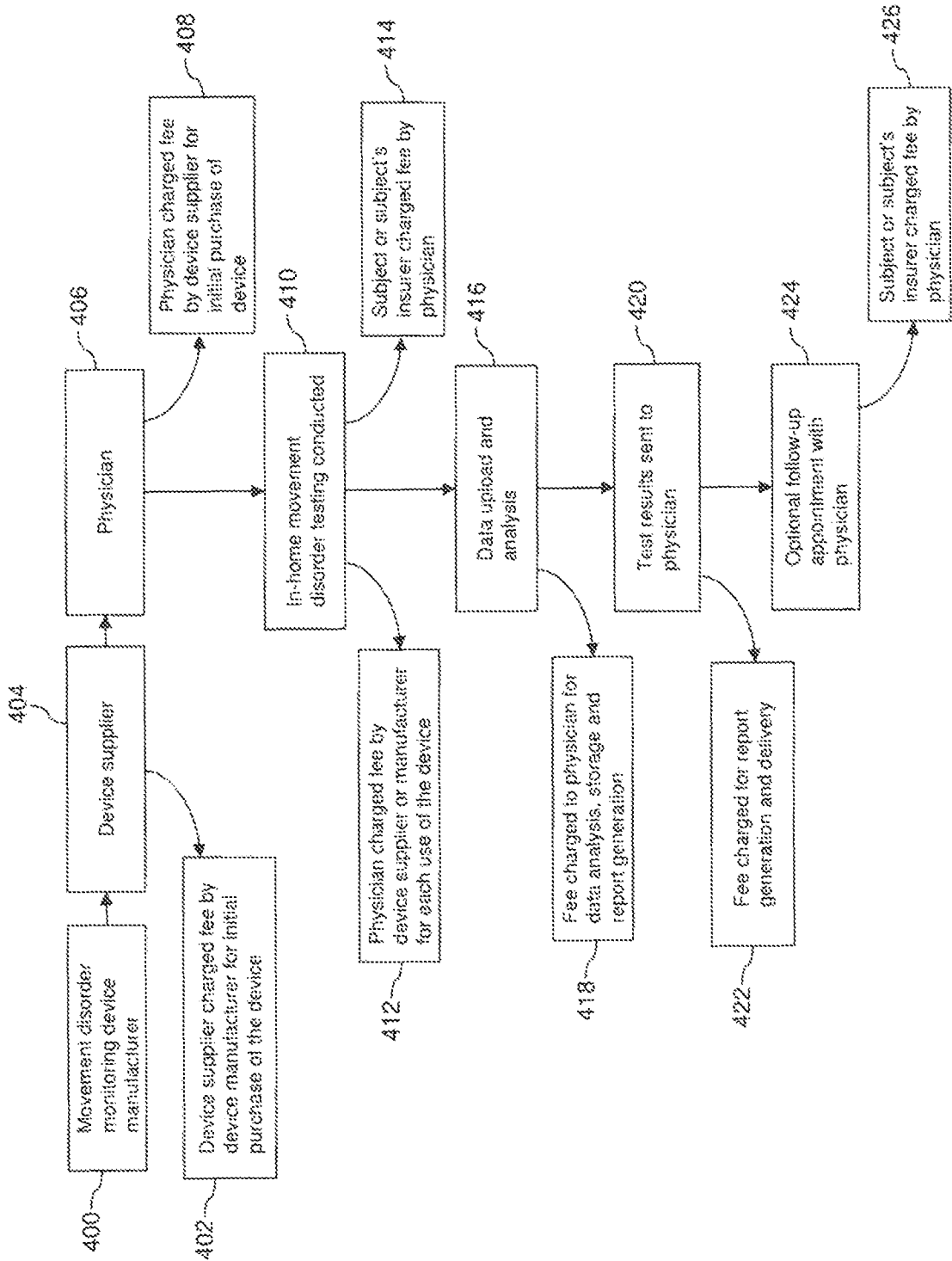
FIG. 11 A flow chart depicting the significant steps associated with one method of the present invention and further showing at which steps charging of fees or billing occurs in using the device of the present invention in a clinical setting.

FIG. 11 includes a flow diagram depicting the significant steps associated with one method included within the scope of the present invention and further shows at which steps charging of fees or billing occurs in using the device of the present invention in a clinical setting as a way for a physician to gain greater insight into effectively treating a subject's movement disorder symptoms.

In the embodiment of the method of the present invention depicted in FIG. 11, the movement disorder monitoring device is originally produced by the device manufacturer 400. The movement disorder monitoring device manufacturer may sell the movement disorder monitoring device to a supplier 402, 404 with the device supplier 404 subsequently providing the device to a physician 406 for use in, for example, the embodiments described above. Alternatively, the device manufacturer 400 and device supplier 404 may be a single entity, eliminating the need for purchase of the movement disorder monitoring device by the device supplier from the device manufacturer 402. Regardless of which party the physician purchases the device from, the physician 406 may be charged a fee 408 for initial purchase of the movement disorder monitoring device. In certain embodiments this fee may be reduced in exchange for the physician assuming liability for the device. When the movement disorder monitoring device is prescribed by the physician for in-home movement disorder testing 410, a fee may be charged by the physician to the subject or the subject's insurer 414 depending upon a subject's individual circumstances. Additionally, in certain embodiments it may further be preferable that a fee be charged to the physician by the movement disorder monitoring device supplier or manufacturer, for each use of the device to perform in-home movement disorder monitoring 412. Upon completion of in-home movement disorder monitoring, recorded data is uploaded to a database, analyzed and results determined 416 using methods previously described herein. An additional fee may then be charged to the physician, practitioner's group, subject, subject's insurance provider, or a combination of these parties for analysis and storage of the data and/or generation of a report 418. After analysis and determination of results, the results and report are sent to the physician 420 for review by the physician and use in determining changes in treatment for the subject, if any. This is preferably done in the form of a follow-up appointment 424 for which the subject or subject's insurance provider is charged a fee by the physician 426. For the step of generating a report of results and delivering the report and results to the physician 422, a fee may be charged to the physician, the physician's practitioner group, subject, subject's insurance provider or any combination of these parties. In certain preferable embodiments, the steps of analysis, storage, determination of results and report generation and delivery are all controlled by the movement disorder device supplier and/or the device manufacturer. This is preferable in certain embodiments because it provides greater efficiency for the processes involved and allows the steps as described to be condensed. For example, a single fee could be charged at box 412 for the use of the movement disorder device by the physician to conduct in-home movement disorder monitoring, which could include the cost of analysis, diagnosis and report generation and delivery, thus eliminating the need for separate billing steps 418, 422 for these functions.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What we claim is:

1. A therapy device combination for providing and/or adjusting therapy or treatment for a subject's movement disorder symptoms, the system comprising:
   a) a drug dose adapted to be provided to the subject, a drug pump or deep brain stimulation (DBS) device comprising therapy or treatment parameters, the drug pump or DBS device adapted to provide a drug dose or DBS therapy to the subject based on the therapy or treatment parameters;
   b) a movement disorder monitoring device comprising at least one sensor adapted to be applied to the subject over a period of time, the at least one sensor further adapted for acquiring movement data corresponding to at least one of the subject's extremities and to be in wired or wireless communication with at least one first processor, and the movement disorder monitoring device further comprising the least one first processor and a memory, the at least one first processor adapted to process and analyze data collected with the at least one sensor and further to quantify severity of the subject's movement disorder symptoms;
   c) a database in communication with the movement disorder monitoring device or an algorithm based on the database and adapted to receive the acquired movement data and/or quantified symptom severity from the movement disorder monitoring device;
   d) the least one processor or a second processor adapted to analyze the movement data and/or quantified symptom severity and to determine an efficacy of the drug dose or drug pump or DBS therapy or treatment parameters at alleviating the subject's movement disorder symptoms and to determine whether the drug dose or drug pump or DBS device therapy or treatment parameters should be changed; and
   e) a system output comprising a new drug dose or therapy or treatment parameters for the drug pump or DBS device based at least in part on the results of the analysis.

2. The therapy device combination of claim 1, wherein the movement disorder monitoring device further comprises a subject interface adapted to enable the subject to input or record a journal or diary entry at the subject's discretion.

3. The therapy device combination of claim 2, wherein the at least one processor of the movement disorder monitoring device is further adapted to communicate wirelessly with software or algorithms on the database to compare and/or correlate the movement data, quantified symptom severity, and/or journal or diary entry with the data on the database.

4. The therapy device combination of claim 1, wherein the system output further comprises a report comprising the acquired movement data, quantified symptom severity, and/or journal or diary entry, or data related to one or more of the movement data, quantified symptom severity, and/or journal or diary entry, and the at least one first and/or second processors are adapted to generate the report via software and to index and display the report data relative to time for viewing and/or analysis by a clinician, physician, and/or the subject to provide an ordered measure of how the data or a subject's symptoms change over time.

5. The therapy device combination of claim 4, wherein the system output comprising a new drug dose or therapy or treatment parameters for the drug pump or DBS device is adapted to instruct and enable a clinician, physician, or the subject to adjust the drug dose or the drug pump or DBS device therapy or treatment parameters based at least in part on the time-indexed report to provide accurate adjustment, efficient optimization of treatment results, and/or to ensure a more constant level of treatment efficacy.

6. The therapy device combination of claim 5, wherein the time-indexed report comprises a two-dimensional table, with time on one axis of the table and movement disorder assessment tasks on the other axis of the table and spaces in the table are then filled with a value that represents the severity of a subject's movement disorder symptom at a given time and with respect to a given movement disorder assessment task.

7. The therapy device combination of claim 6, wherein the at least one sensor is adapted to be applied to, worn upon, or otherwise affixed to the subject's wrist.

8. A therapy device combination for providing and/or adjusting therapy or treatment for a subject's movement disorder symptoms, the system comprising:
   a) a drug dose adapted to be provided to the subject, a drug pump or deep brain stimulation (DBS) device comprising therapy or treatment parameters, the drug pump or DBS device adapted to provide a drug dose or DBS therapy to the subject based on the therapy or treatment parameters;
   b) a movement disorder monitoring device comprising at least one sensor adapted to be applied to the subject over a period of time, the at least one sensor further adapted for acquiring movement data corresponding to at least one of the subject's extremities and to be in wired or wireless communication with at least one first processor, and the movement disorder monitoring device further comprising the at least one first processor, the processor adapted to store data, to correlate data between the movement disorder monitoring device and external devices, and further to quantify severity of the subject's movement disorder symptoms;

c) the least one processor or a second processor adapted to analyze the analyzing the movement data and/or quantified symptom severity to determine an efficacy of the drug dose or DBS therapy at alleviating the subject's movement disorder symptoms and to determine whether the drug dose or drug pump or DBS device therapy or treatment parameters should be changed; and d) a system output comprising a new drug dose or therapy or treatment parameters for the drug pump or DBS device based at least in part on the results of the analysis, wherein the movement disorder monitoring device is further adapted to transmit movement data, the quantified symptom severity, and/or data related to the movement data and/or quantified symptom severity to a database in near real-time as data is collected from the subject and the system output further comprises a report comprising the acquired movement data and/or quantified symptom severity, or data related to the movement data or quantified symptom severity, and the at least one first and/or second processors are adapted to generate the report via software and to index and display the report data relative to time for viewing and/or analysis by a clinician, physician, and/or the subject to provide an ordered measure of how the data or a subject's symptoms change over time.

9. The therapy device combination of claim 8, wherein near real-time means that the time between starting of movement disorder monitoring data analysis and generation of the final report is less than 6 hours.

10. The therapy device combination of claim 8, wherein near real-time means that the time between starting of movement disorder monitoring data analysis and generation of the final report is less than 3 hours.

11. The therapy device combination of claim 10, wherein movement disorder monitoring device further comprises a subject interface adapted to enable the subject to input or record a journal or diary entry at the subject discretion.

12. The therapy device combination of claim 11, wherein the at least one processor of the movement disorder monitoring device is further adapted to communicate wirelessly with software or algorithms on the database to compare and/or correlate the movement data, quantified symptom severity, and/or journal or diary entry with the data on the database.

13. The therapy device combination of claim 12, wherein the system output comprising a new drug dose or therapy or treatment parameters for the drug pump or DBS device is adapted to instruct and enable a clinician, physician, or the subject to adjust the drug dose or the drug pump or DBS device therapy or treatment parameters based at least in part on the time-indexed report to provide accurate adjustment, efficient optimization of treatment results, and/or to ensure a more constant level of treatment efficacy.

14. The therapy device combination of claim 13, wherein the at least one sensor is adapted to be applied to, worn upon, or otherwise affixed to the subject's wrist.

15. A therapy device combination for providing and/or adjusting therapy or treatment for a subject's movement disorder symptoms, the system comprising:

a) a drug dose adapted to be provided to the subject, a drug pump or deep brain stimulation (DBS) device comprising therapy or treatment parameters, the drug pump or DBS device adapted to provide a drug dose or DBS therapy to the subject based on the therapy or treatment parameters;

b) a movement disorder monitoring device comprising at least one sensor adapted to be applied to the subject over a period of time, the at least one sensor further adapted for acquiring movement data corresponding to at least one of the subject's extremities and to be in wired or wireless communication with at least one first processor, the and the movement disorder monitoring device further comprising the at least one first processor and a memory, the at least one first processor adapted to process and analyze data collected with the at least one sensor and further to quantify severity of the subject's movement disorder symptoms;

c) a database in communication with the movement disorder monitoring device or an algorithm based on the database and adapted to receive the movement data and/or quantified symptom severity from the movement monitoring device;

d) the least one processor or a second processor adapted to analyze the movement data and/or the quantified symptom severity and to determine an efficacy of the drug dose or drug pump or DBS therapy or treatment parameters at alleviating the subject's movement disorder symptoms and to determine whether the drug dose or drug pump or DBS therapy or treatment parameters should be changed; and h) a system output comprising a new drug dose or therapy or treatment parameters for the drug pump or DBS device based at least in part on the results of the analysis, wherein the movement disorder monitoring device is adapted to transmit preprocessed movement data and/or quantified symptom severity to the data base in near real-time as data is collected from the subject.

16. The therapy device combination of claim 15, wherein the movement disorder monitoring device further comprises a subject interface adapted to enable the subject to input or record a journal or diary entry at the subject's discretion.

17. The therapy device combination of claim 16, wherein near real-time means that the time between starting of movement disorder monitoring data analysis and generation of the final report is less than 6 hours.

18. The therapy device combination of claim 16, wherein near real-time means that the time between starting of movement disorder monitoring data analysis and generation of the final report is less than 3 hours.

19. The therapy device combination of claim 18, wherein the at least one processor of the movement disorder monitoring device is further adapted to communicate wirelessly with software or algorithms on the database to compare and/or correlate the movement data, quantified symptom severity, and/or journal or diary entry with the data on the database.

20. The therapy device combination of claim 19, wherein the system output comprising a new drug dose or therapy or treatment parameters for the drug pump or DBS device is adapted to instruct and enable a clinician, physician, or the subject to adjust the drug dose or the drug pump or DBS device therapy or treatment parameters based at least in part on the time-indexed report to provide accurate adjustment, efficient optimization of treatment results, and/or to ensure a more constant level of treatment efficacy.

* * * * *